(12) United States Patent
van Dyke, Jr. et al.

(10) Patent No.: US 6,202,829 B1
(45) Date of Patent: Mar. 20, 2001

(54) CONVEYOR SYSTEM FOR CLINICAL TEST APPARATUS

(75) Inventors: Bingham Hood van Dyke, Jr., Gilbertsville, PA (US); John Louis Barra, Glendora, NJ (US); Thomas James Hatcher, Malver, PA (US); Michael John Campanelli, Mahopac, NY (US)

(73) Assignee: Bayer Corporation, Tarrytown, NY (US)

(*) Notice: Subject to any disclaimer, the term of this patent is extended or adjusted under 35 U.S.C. 154(b) by 0 days.

(21) Appl. No.: 09/575,589

(22) Filed: May 22, 2000

Related U.S. Application Data

(60) Division of application No. 09/115,014, filed on Jul. 14, 1998, which is a continuation-in-part of application No. 08/970,549, filed on Nov. 14, 1997, now Pat. No. 6,024,204.

(51) Int. Cl.$^7$ .................................................. B65G 25/00
(52) U.S. Cl. .................. 198/465.2; 198/379; 198/349.6; 198/459.7
(58) Field of Search ............................. 198/465.2, 459.7, 198/349.6, 379

(56) References Cited

U.S. PATENT DOCUMENTS

| | | | |
|---|---|---|---|
| 2,341,705 | * | 2/1944 | Fedorchak et al. . |
| 2,632,553 | * | 3/1953 | Stirn et al. . |
| 3,101,848 | * | 8/1963 | Uhlig . |
| 3,814,232 | * | 6/1974 | Eriksson ................................ 198/379 |
| 4,163,537 | | 8/1979 | Mourgue . |
| 4,635,801 | | 1/1987 | Oren . |
| 4,715,488 | | 12/1987 | Hewitt et al. . |
| 4,961,553 | | 10/1990 | Todd . |
| 5,186,314 | | 2/1993 | Clopton . |
| 5,657,854 | | 8/1997 | Chen et al. . |
| 5,855,342 | | 1/1999 | Hawkins et al. . |
| 5,966,309 | * | 10/1999 | O'Bryan et al. ................ 364/478.13 |
| 6,024,204 | * | 2/2000 | van Dyke, Jr. et al. .......... 198/459.6 |
| 6,056,106 | * | 5/2000 | van Dyke, Jr. et al. .......... 198/346.1 |

* cited by examiner

Primary Examiner—Christopher P. Ellis
Assistant Examiner—Richard Ridley
(74) Attorney, Agent, or Firm—Andrew L. Klawitter, Esq.; Rodman & Rodman

(57) ABSTRACT

The conveyor system for clinical test apparatus includes a main transport conveyor and a plurality of auxiliary conveyors located alongside the main transport conveyor. The auxiliary conveyors define straight line paths of travel parallel to the straight line paths of travel of the main conveyor. Each of the auxiliary conveyors is operated by drive means separate from the main transport conveyor. Two crossover points are provided between the main transport conveyor and the auxiliary conveyor. One crossover point is an entrance from the main transport conveyor to the auxiliary conveyor and the other crossover point is an exit from the auxiliary conveyor to the main transport conveyor. Each crossover point is controlled by a gate. One of the gates is a divert gate which can be actuated to block the main transport path thereby diverting puck traffic onto the auxiliary conveyor. The other gate is an interface gate which is used primarily to read information on a sample tube before it is introduced into a test apparatus and also functions as a load and unload station for the clinical test apparatus. The conveyor system also has a main unload and load system wherein tubes that have been completely tested are removed from pucks and reloaded with new tubes that are to be tested.

2 Claims, 24 Drawing Sheets

CONVEYOR SYSTEM FOR CLINICAL TEST APPARATUS

BACKGROUND OF THE INVENTION

This application is a continuation-in-part of application Ser. No. 08/970,549 filed Nov. 14, 1997 now U.S. Pat. No. 6,024,204. Also this application is a Division of Ser. No. 09/115,014 filed Jul. 14, 1998.

This invention relates to conveyor devices for transporting biological material in containers to clinical test apparatus and more particularly to a conveyor system with a main transport lane for all containers to be tested and individual sidebar lanes associated with different clinical test apparatus, and traffic control gates at each sidebar lane for diverting separate groups of containers to their corresponding clinical test apparatus. The invention further relates to a system for supporting utility installations for the conveyor and its associated traffic control gates.

The term "clinical testing" is intended to refer to hematological tests, tests relating to immunoassay, toxicology, urinalysis and any other specific category of testing performed on biological or body material such as blood, serum, and urine for example. The clinical testing of blood, serum, urine or other body fluid provides invaluable information relative to the health status of an individual and clinical test results are commonly used for diagnostic evaluation, surgical decision making and the recognition of when a change or changes have occurred in a patient's health status.

Clinical testing often involves esoteric and costly procedures that must produce quality information with a high degree of accuracy. As new clinical tests are conceived and conventional clinical tests are improved, the expanding pool of information that is obtainable from various clinical tests must be weighed against the cost of obtaining such information. By reducing the cost of clinical tests, such tests can have the widest possible availability to those individuals who would benefit most from the tests.

One known way of reducing the costs for clinical testing is to perform such tests automatically and as quickly as possible. Thus diverse clinical test apparatus have been developed which operate independently of each other to perform different types of specialized tests with a minimal amount of personnel. The tests are usually performed on fluid samples that are contained in sample tubes, although other containment formats are also used, especially when the test material is not in fluid form.

However separate personnel and supervision teams are generally required to oversee each individual clinical test apparatus and separate work areas are often required for each specific category of clinical test apparatus. Thus, a laboratory which is engaged in diverse clinical testing procedures would require a relatively large facility space to accommodate the separate clinical test apparatus.

In a further attempt to reduce operating costs for clinical testing a common transport system has been developed to automatically deliver test material containers such as sample tubes to a variety of otherwise unrelated and independent clinical test apparatus. Such transport system includes a conveyor adapted to run along a predetermined travel path with different, unrelated clinical test apparatus located along the travel path of the conveyor. Each of the clinical test apparatus is adapted to operate on a common sample tube that is transported by the conveyor system.

The known conveyor systems for delivering sample tubes to different clinical apparatus are usually custom built for the particular needs of a test laboratory. In many instances the construction of conveyor systems for clinical test apparatus require dedicated installations of electrical power supply, plumbing service, vacuum and pressure service. Thus the known conveyor systems usually have the character of custom design, permanency and inflexibility once they are installed.

It is thus desirable to provide a conveyor system for clinical testing of biological materials in containers, which conveyor system can be constructed with modular stations for each clinical test apparatus, with simplified installations for plumbing, electricity, vacuum and pressure service that do not require ground, wall or ceiling installation.

OBJECTS AND SUMMARY OF THE INVENTION

Among the several objects of the invention may be noted the provision of a novel conveyor system for clinical test apparatus, a novel conveyor system that has a main transport lane and one or more auxiliary lanes corresponding to each clinical apparatus, a novel conveyor system for clinical test apparatus wherein auxiliary transport lanes are provided alongside main transport lanes for side by side movement of sample tubes on a main transport lane and on an auxiliary transport lane, a novel conveyor system for clinical test apparatus including a main transport conveyor and a plurality of separately run auxiliary conveyors, and wherein each auxiliary conveyor is associated with a separate clinical test apparatus, a novel conveyor system wherein each auxiliary conveyor is provided with traffic control gates including a diverter gate and an interface gate wherein the diverter gate selectively diverts sample tubes from the main transport conveyor to the auxiliary conveyor and the interface gate controls return of the diverted sample tubes to the main transport conveyor, a novel conveyor system for clinical test apparatus that also carries its own utility service lines such as electrical, plumbing, pressure and vacuum lines, a novel system for supporting the utility service lines, a novel conveyor system for clinical test apparatus wherein the main transport conveyor is separately driven by one motor while the auxiliary transport conveyors are each driven by separate motors, and novel gates for directing sample tubes to selected clinical apparatus for testing or other functional purpose.

Other objects and features of the invention will be in part apparent and in part pointed out hereinafter.

In accordance with the present invention, the conveyor system for clinical test apparatus includes a main transport conveyor that defines a closed circuit travel path. The closed circuit travel path permits objects that remain on the conveyor to repeat the travel path when the conveyor moves in one direction. The main transport conveyor has straight line paths and curved paths. The conveyor system also includes a plurality of auxiliary conveyors that define a straight line travel path. The auxiliary conveyors, which are arranged in series with one another are located alongside the straight line travel paths of the main transport conveyor. Each auxiliary conveyor transports an object from one end of the auxiliary conveyor to the other end without retracing any point of travel when the auxiliary conveyor is moving in one direction, which is normally the same direction as the main transport conveyor.

Each of the auxiliary conveyors are controlled by separate motors or drive means that are preferably independent of the motor or drive means for the main transport conveyor. In this manner the auxiliary conveyors can be arranged as modules alongside the main transport conveyor.

Separation means are provided between the main transport conveyor and the auxiliary conveyor except at predetermined intersections between the main transport conveyor and the auxiliary conveyor. Such intersections are defined by gate controlled crossover openings that permit diversion of sample tubes from the main transport conveyor to the auxiliary conveyor and vice versa.

One of the gate openings is controlled by a divert gate device which has actuatable diversion means for diverting movement of objects on the main transport conveyor to the auxiliary conveyor. The diversion means has one position that blocks off the flow of traffic on the main transport conveyor and at the same time directs such traffic to the auxiliary conveyor. The diversion means has another position that does not interfere with traffic on the main transport conveyor and thus permits such traffic to bypass the auxiliary conveyor.

Another crossover opening that provides a direct flow path from the auxiliary conveyor to the transport conveyor is controlled by an interface gate device that is located upstream of the crossover opening. The interface gate device as well as the divert gate device cooperate with label readers for the sample tubes. The sample tubes are thus rotated at each gate device to enable the label reader to obtain a reading of the sample tube label.

A clinical test apparatus or other functional device which operates on the sample tubes is associated with each auxiliary conveyor. Thus one auxiliary conveyor can be associated with a load and unload station for the sample tubes. Other auxiliary conveyors are respectively associated with different clinical test apparatus that perform different categories of tests on sample tubes.

If a sample tube is to be tested by a specific clinical test apparatus the system programming and the information on the individual sample tube label will cause activation of the gates in a manner which will direct the sample tube to the intended clinical test apparatus while enabling sample tubes that are not intended to be tested by a clinical test apparatus to bypass the auxiliary conveyor associated with that clinical test apparatus. Thus the sample tubes will go only to a clinical test apparatus that is to perform a required test on the sample tube.

Sample tubes are unloaded from pucks when they are to be tested by a clinical test apparatus. The empty puck is reloaded with another sample tube that is exiting from the test apparatus. Thus the puck remains on the conveyor during unloading and reloading of sample tubes. The unloading and reloading of the pucks is accomplished by a robotic device that forms no part of the present invention.

Although the main transport conveyor and the auxiliary transport conveyors are separately driven and each clinical test apparatus operates independently of the other clinical test apparatus, the movement of all sample tubes and the operation of all the gates in the conveyor system is governed by a single process control means such as a computer.

Columns which support the conveyor system also support utility service for the conveyor system such as electrical lines, plumbing lines, air pressure lines and vacuum lines. The installation of such utility lines above ground and on the conveyor columns facilitates servicing and construction of the conveyor system.

The invention accordingly comprises the constructions hereinafter described, the scope of the invention being indicated in the claims.

DESCRIPTION OF THE DRAWINGS

In the drawings.

Corresponding reference characters indicate corresponding parts throughout the several views of the drawings.

DETAILED DESCRIPTION OF THE INVENTION

A conveyor system for clinical test apparatus incorporating one embodiment of the invention is generally indicated by the reference number 10.

Figure 1:
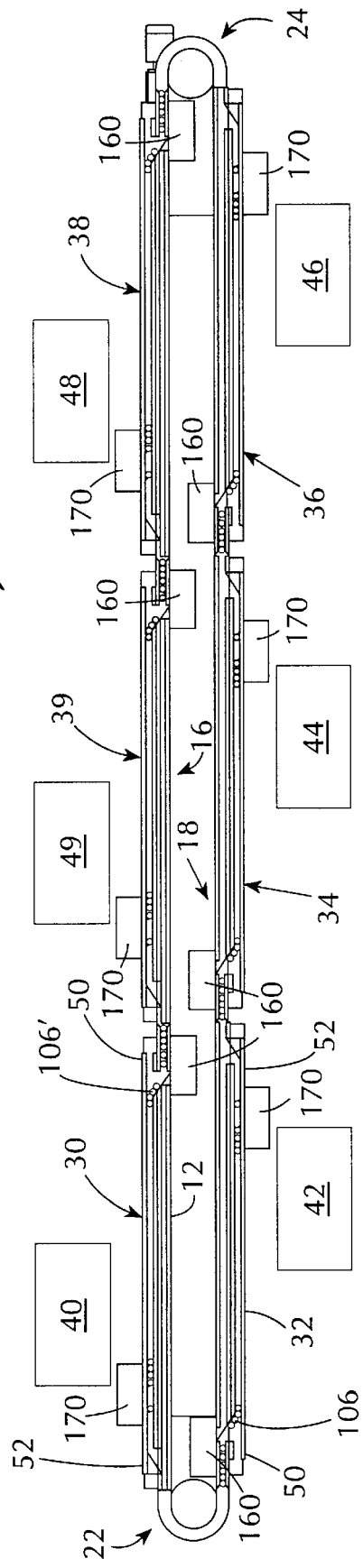
FIG. 1 is a simplified schematic plan view of a conveyor system incorporating the present invention.

Referring to FIG. 1 the conveyor system 10 includes a main transport conveyor 12 defining a closed circuit travel path in a generally horizontal plane. The closed circuit travel path permits objects that remain on the conveyor 12 to repeat the path of travel when the conveyor 12 is moving in one direction. The closed circuit travel path includes two straight line paths 16 and 18 and two curved paths 22 and 24 at respective opposite ends of the straight line paths 16 and 18.

An auxiliary conveyor 30, which has a straight line travel path, is positioned alongside and parallel to the straight line travel path 16 of the main transport conveyor 12. The straight line travel path of the auxiliary conveyor 30 permits objects on the conveyor 30 to move from one point to another without retracing any point of travel when the conveyor 30 is moving in one direction.

The auxiliary conveyor 30 is associated with a load and unload station 40 that represents an initial and final transport point for sample tubes 106. Robots (not shown) at the station 40 remove tested sample tubes 106 from the conveyor 30 and replaces them with new sample tubes 106 to be tested. An auxiliary conveyor 32 is associated with a clinical test apparatus station 42 which performs a specific category of tests on a sample tube 106. Additional auxiliary conveyors 34, 36, 38 and 39, similar to the conveyors 30 and 32 are also provided alongside and parallel to the straight line paths 16 and 18 of the conveyor 12 in series with the auxiliary conveyors 30 and 32. Each auxiliary conveyor 34, 36, 38 and 39 is associated with a clinical test apparatus station such as 44, 46, 48 and 49 that perform separate and distinct categories of clinical tests. However the auxiliary conveyors 30–39 associated with the different stations 40–49 are generally similar in operation and construction.

The main transport conveyor 12 is arranged to run in a counterclockwise direction, although the direction of travel is a matter of choice. The auxiliary conveyor 30, and all other auxiliary conveyors 32–39 preferably run in the same direction as the main transport conveyor 12. The auxiliary conveyor 30, which has an upstream end 50 and a downstream end 52, travels in a generally horizontal plane that is preferably coplanar with the travel plane of the main transport conveyor 12. Pairs of gate devices 160 and 170 are provided on the conveyor system 10 between opposite ends 50 and 52 of any of the auxiliary conveyors 30–39.

Figure 2:
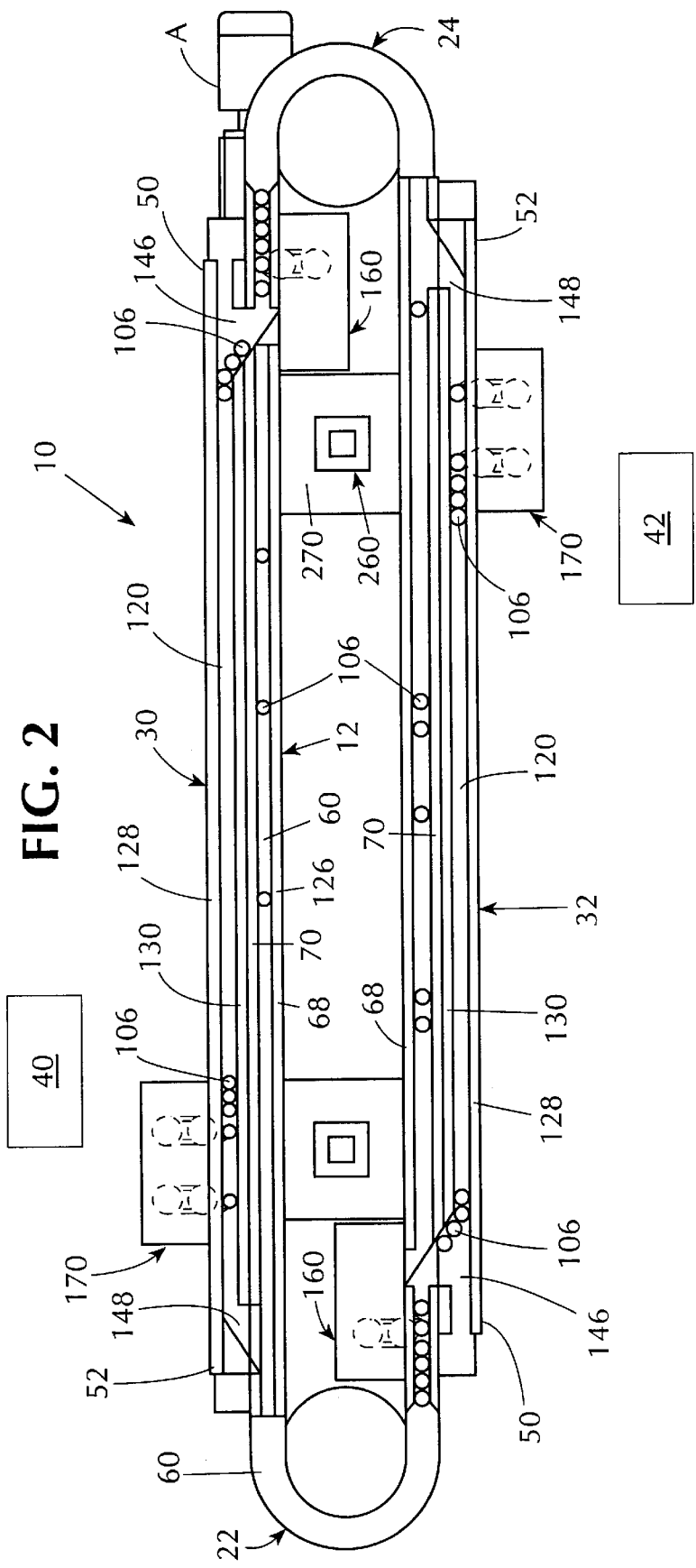
FIG. 2 is an enlarged simplified schematic plan view thereof with a reduced number of auxiliary conveyors.
Figure 3:
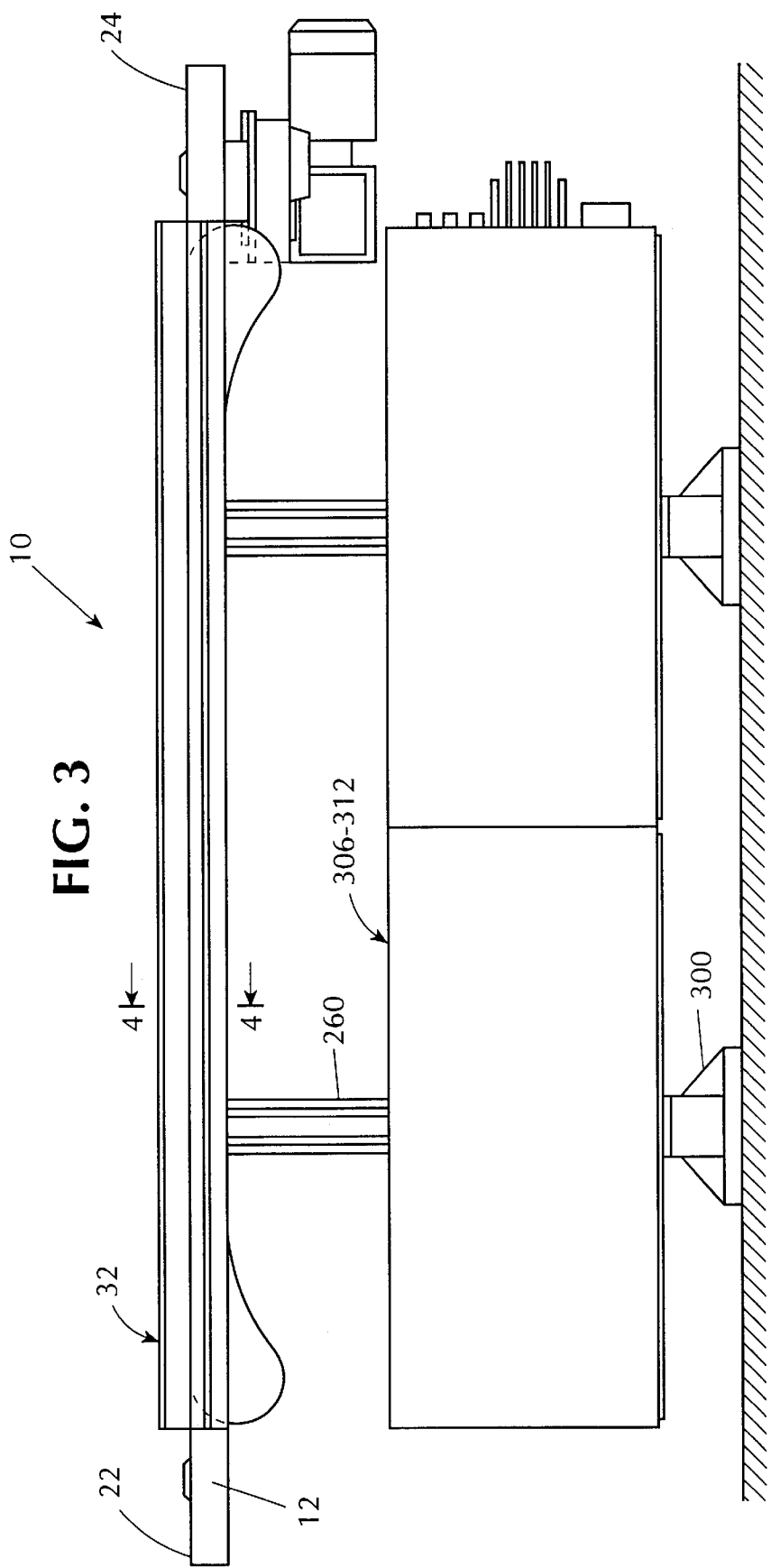
FIG. 3 is a front elevational view thereof.

For purposes of clarity, reference will be made to a simplified conveyor system as shown in FIG. 2 which has the same operating structures as the conveyor system 10 of FIG. 1, but is more clearly illustrated on a larger scale than that of FIG. 1.

The main transport conveyor 12 includes a known conveyor belt 60. The conveyor belt 60 defines a main transport lane also indicated by the reference number 60 since the main transport lane is the path traveled by objects on the conveyor belt 60. The conveyor belt 60 is bordered at opposite sides by edge walls 68 and 70 that are generally mirror images of each other. The edge walls 68 and 70 include ledge portions 76 and 78 (FIG. 4) located at a predetermined height above the conveyor belt 60 and projecting over the conveyor belt 60. The ledge portions 76 and 78 cooperate with the conveyor belt 60 to form a vertical confinement for generally cylindrical sample tube pucks 100 that travel on the conveyor belt 60 and hold a sample tube 106, which can be of different heights and diameter within a predetermined size range such as approximately 13 to 16 mm in diameter and 75 to 100 mm in height.

The puck 100 includes resilient biasing means 104 (FIG. 6) which apply a slight retention force on the sample tube 106. The puck 100 maintains a stable positioning of the sample tube 106 as the conveyor belt 60 transports the puck 100 from one location to another along the conveyor belt travel path. The biasing means 104 in the puck 100 permits removal and replacement of the sample tube 106 in the puck 100 as often as is necessary. As used herein the term sample tube 106 is generally intended to include the puck 100 which holds the sample tube 106, unless otherwise indicated.

The auxiliary conveyor 30 includes a known conveyor belt 120. The conveyor belt 120 defines a sidebar lane also indicated by the reference number 120 since the sidebar lane is the path traveled by objects on the conveyor belt 120. The conveyor belt 120 is bordered on opposite sides by edge walls 128 and 130 (FIG. 4) similar to the edge walls 68 and 70. The edge walls 128 and 130 include ledge portions 136 and 138 which perform the same function as the ledge portions 76 and 78.

Figure 4:
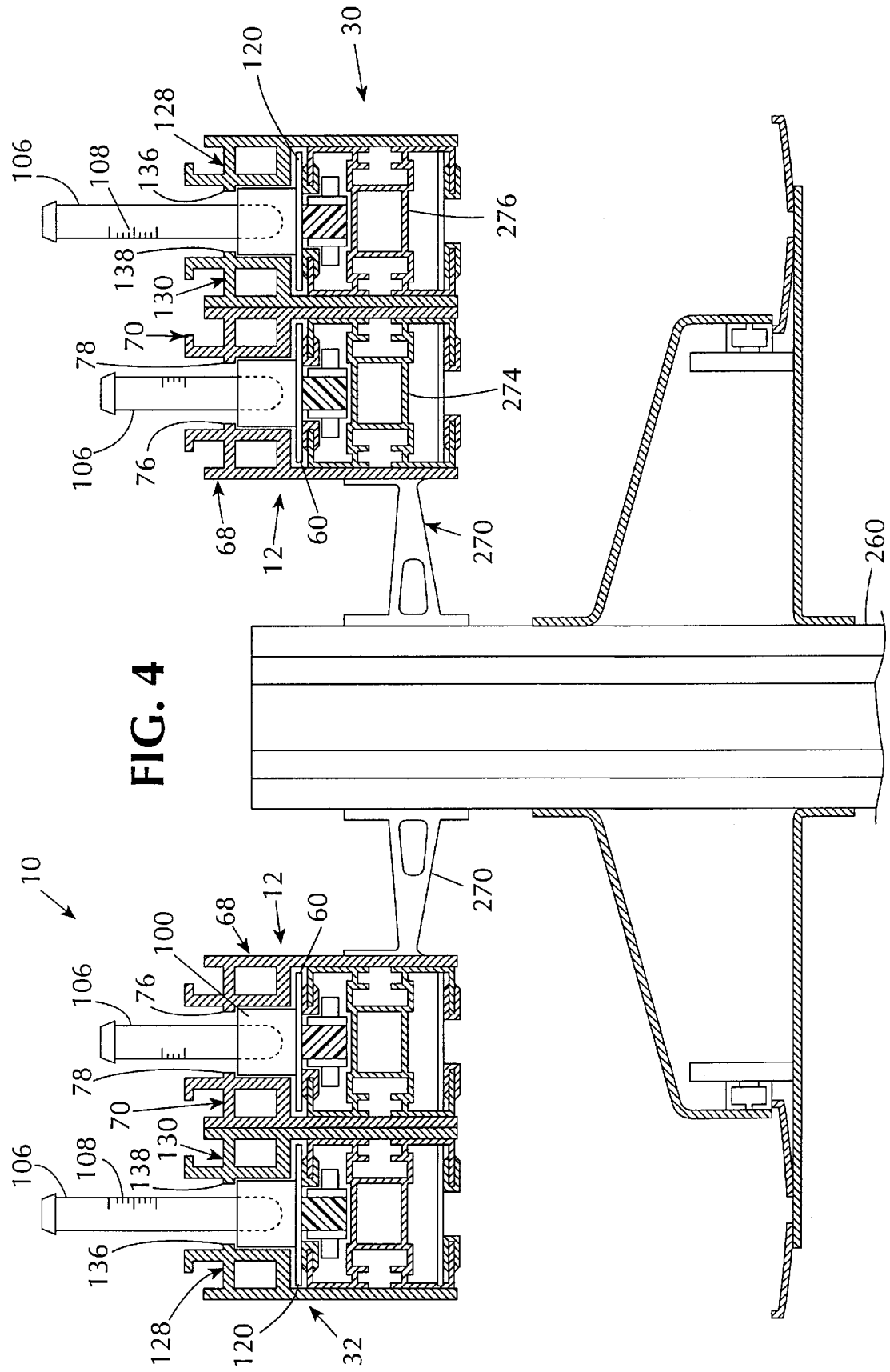
FIG. 4 is a sectional view thereof taken on the line 4—4 of FIG. 3.

As most clearly shown in FIG. 4 the edge walls 70 and 130 are located adjacent each other between the edge walls 68 and 128. The adjacent edge walls 70 and 130 function as a separation or segregation means between the main transport lane 60 and the sidebar lane 120. The adjacent edge walls 70 and 130 include a sidebar entrance opening 146 (FIG. 2) proximate the upstream end 50 of the auxiliary conveyor 30 and a sidebar exit opening 148 proximate the downstream end 52 of the auxiliary conveyor 30. The entrance opening 146 and the exit opening 148 are also referred to as traffic intersections that are controlled by the gate devices 160 and 170.

The gate device 160, which is also referred to as a divert gate, is provided at the edge wall 68 of the transport conveyor 12 in substantial alignment with the sidebar entrance opening 146 at the upstream end 50 of the auxiliary conveyor 30. The gate device 170 which is also referred to as an interface gate is provided alongside the edge wall 128 of the auxiliary conveyor 30 a short distance upstream of the sidebar exit opening 148.

In order to efficiently control puck traffic at the intersections 146 and 148 between the main transport lane 60 and any of the sidebar lanes 120 the gate devices 160 and 170 must obtain a reading of information pertaining to each sample tube 106 passing through the gate device. Subsequent action on the sample tube 106 including a determination of the travel path, and the unloading and/or loading of the sample tubes 106 in the pucks 100 will be based on the information that is read from the sample tube 106 at the gates 160 and 170.

Figure 7:
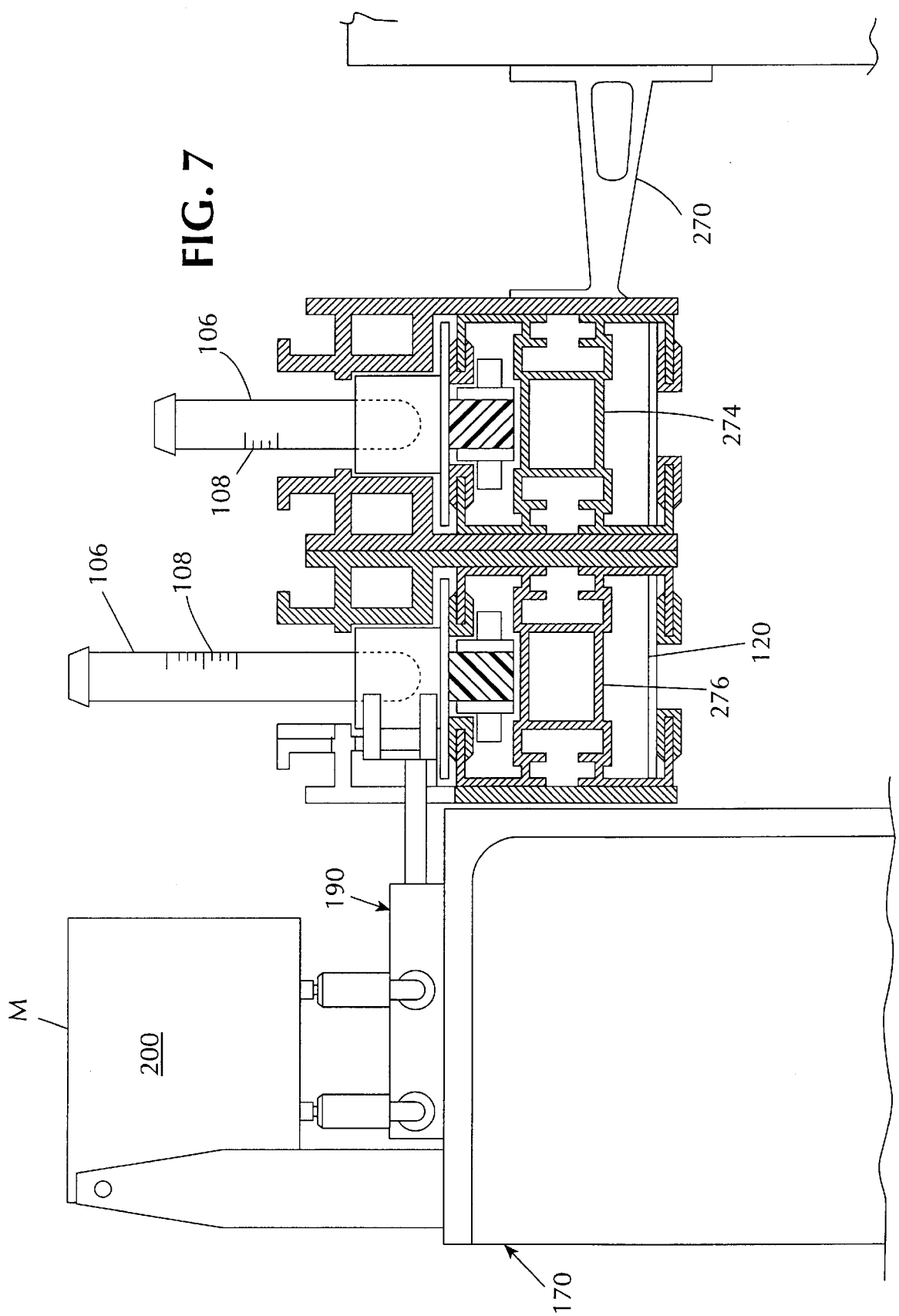
FIG. 7 is a sectional view taken on the line 7—7 of FIG. 6.

Each sample tube 106 is a reservoir of sample fluid that is later extracted or withdrawn from the sample tube at the clinical test apparatus in selected quantities for whatever tests are to be performed by one or more clinical test apparatus. Each sample tube 106 thus includes a label 108 (FIG. 7) with information relating to the identity of the individual supplying the test sample, the type of fluid in the sample tube and the type of test or tests that are to be performed on the material contained in the sample tube, hereinafter referred to as the label information. Under this arrangement each sample tube 106 is uniquely distinguishable from other sample tubes and can be individually identified. The label 108 applied to the sample tube 106 is preferably in a machine readable format such as a known bar code that can be automatically read or interpreted in a known manner by a known label reading device.

Thus a label reader device at the gates 160 and 170 will read the sample tube label and communicate the label information to a system control computer (not shown) that governs all processing operations performed by the conveyor system 10 and also governs the acceptance of the sample tubes 106 by the respective clinical test apparatus. The process control computer thus retains the label information and process activity information for each sample tube 106. This information is specifically used to control the gate devices 160 and 170 to direct the sample tube 106 to the appropriate clinical test apparatus in accordance with known programming techniques.

With regard to the control of puck traffic at the auxiliary conveyor 30, the divert gate 160 (FIG. 5) includes three pneumatically controlled plunger devices 180, 182 and 184 of known construction supported on a gate housing 186. The plunger devices 180 and 182 respectively include retractable fingers 192 and 194, and the plunger device 184 includes a retractable divert head 196 with an inclined surface 198. A puck rotating mechanism 190 is provided on the gate housing 186 between the plunger devices 180 and 182 to rotate the puck 100 and the sample tube 106 to allow the sample tube label 108 to be read by a known label scanner or reader device 200 (FIG. 7) shown at the gate 170 but also provided at the gate 160.

Figure 5:
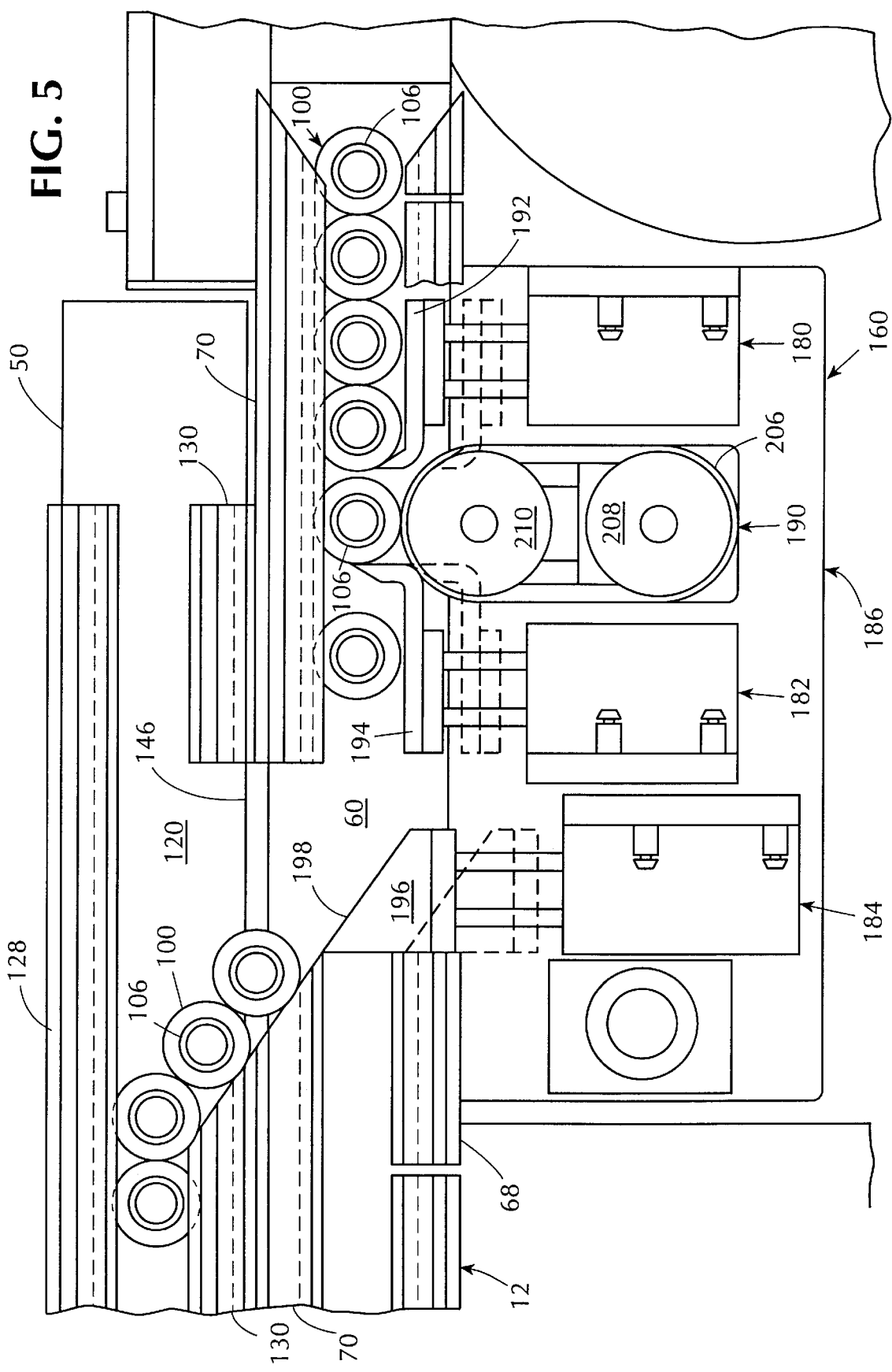
FIG. 5 is an enlarged schematic plan view of a divert gate device employed in the conveyor system.

When the respective fingers 192 and 194 of the plunger devices 180 and 182 are in a protracted position as shown in FIG. 5 the combination of the plunger devices 180 and 182 with the puck rotating mechanism 190 constitute a singulator device that enables the label reader device 200 to read the label of one sample tube 106 at a time. The retractable fingers 192 and 194 are spaced apart a distance slightly larger than the puck diameter to permit the puck rotating mechanism 190 to rotate the puck 100 between the protracted fingers 192 and 194.

The puck rotating mechanism 190, which can be automatically controlled in a known manner for slight lateral movement toward and away from the main transport lane 60, includes a puck contacting belt 206 driven by wheels 208 and 210. When a singulated sample tube 106 has been read by the reader device 200, the finger 194 retracts to permit the singulated sample tube 106 to move toward the plunger device 184. The finger 192 remains protracted to hold back the non-singulated sample tubes 106. The protracted or retracted position of the divert head 196 will determine whether the singulated sample tube 106 stays on the main transport lane 60 or is diverted to the sidebar lane 120. Retracted positions of the fingers 192, 194 and the divert head 196 are shown dotted in FIG. 5.

If all testing has been completed for the singulated sample tube 106 the divert head 196 (FIG. 5) will be protracted to block off the main transport lane 60. The singulated sample tube 106 will thus be diverted to the sidebar lane 120 of the auxiliary conveyor 30, which leads to the load/unload station 40. Completely tested singulated sample tube 106 will travel on the sidebar lane 120 to the interface gate 170. If further testing is required for the singulated sample tube 106 the divert head 196 will be retracted to enable the sample tube 106 to remain on the main transport lane 60 and thereby bypass the auxiliary conveyor 30 and the load/unload station 40.

When another sample tube 106 is to be singulated for label reading at the divert gate 160 the finger 194 is protracted and the finger 192 is retracted to permit the line of sample tubes 106 to proceed to the finger 194. The finger 192 is then protracted to singulate the next sample tube 106.

The interface gate 170 (FIG. 6) includes three pneumatically controlled plunger devices 220, 222 and 224 of known construction supported on a gate housing 226. The plunger devices 220, 222 and 224 respectively include retractable fingers 232, 234 and 236. Retracted positions of the fingers 232, 234 and 236 are shown dotted in FIG. 6.

One puck rotating mechanism 242, similar to the puck rotating mechanism 190 is supported on the gate housing 226 between the plunger devices 220 and 222 and another puck rotating mechanism 244, similar to the puck rotating mechanism 190 is supported on the gate housing 226 between the plunger devices 222 and 224. The combination of the plunger devices 220 and 222 with the puck rotating mechanism 242 constitute a singulator device that enables the label reader device 200 at the gate 170 (FIG. 7) to read the label 108 of one sample tube 106 at a time, in the same manner as described for the singulator device at the divert gate 160.

The completely tested sample tube 106 is thus lined up with other sample tubes 106 behind the protracted finger 234 of the plunger device 222 at the interface gate 170 while the finger 232 of the plunger device 220 is retracted. The retracted finger 232 of the plunger device 220 is then protracted to singulate sample tube 106, wherein the sample tube 106 is confined between the fingers 232 and 234 for rotation by the puck rotating mechanism 242. The label 108 (FIG. 7) on the rotating sample tube 106 is read by the reader device 200. The process or system control computer (not shown) that is linked to each of the label reader devices 200 maintains a history of the test activity for each and every sample tube 106 and a record of all testing not yet performed on any sample tube.

If there is a confirmation at the interface gate 170 that all testing has been completed for a singulated sample tube 106 as determined during the label reading operation at the puck rotating mechanism 242, then the sample tube 106 is withdrawn from the puck 100 by a robot (not shown) while the puck 100 is singulated at the puck rotating mechanism 242. The unloaded puck 100 with exposed biasing spring 104 (FIG. 6) remains on the auxiliary conveyor 30 due to the vertical confinement provided by the ledges 136 and 138 (FIG. 4) at the conveyor edge portions 128 and 130.

The unloaded puck 100 (FIG. 6) is then allowed to pass beyond the singulation point by retraction of the finger 234. The unloaded puck 100 is held from further movement by the protracted finger 236 at the plunger device 224. A robot (not shown) places a new sample tube 106 in the unloaded puck 100 while the puck is restrained by the finger 236. The new sample tube 106 in the reloaded puck 100 is rotated by the rotating mechanism 244 to permit an initial reading of test instructions and sample identification from the label of the new sample tube 106. The rotating mechanisms 242 and 244 can have separate drive means or be commonly driven from a single drive means.

The finger 236 of the interface gate 170 is then retracted to permit the new sample tube 106 to proceed through the sidebar exit opening 148 (FIG. 2) to transfer from the sidebar lane 120 of the auxiliary conveyor 30 to the main transport lane 60. Other pucks 100 that are lined up for singulation at the interface gate 170 of the auxiliary conveyor 30 are similarly processed for reading of their respective sample tube labels. Thus, sample tubes 106 at the interface gate 170 of the auxiliary conveyor 30 will be unloaded if their testing is completed or allowed to pass beyond the gate 170 if further testing is indicated by the label reader 200.

The newly loaded sample tubes 106 and the older retained sample tubes 106 that still require further testing pass through the interface gate 170 (FIG. 2) at the load/unload station 40 and exit at the exit opening 148 from the auxiliary conveyor 30 to the main transport lane 60. The main transport lane 60 carries the sample tubes 106 to the divert gate 160 at the intersection of the auxiliary conveyor 32 and the main transport lane 60. The sample tubes 106 are initially held in line at the divert gate 160 by the protracted finger 194 (FIG. 5). The sample tubes 106 are then singulated for label reading in a manner similar to that previously described for the divert gate 160 at the auxiliary conveyor 30.

When the label of a singulated sample tube 106 has been read the process computer receives the information and will cause the plunger device 184 to protract the divert head 196 if the sample tube 106 is to be tested by the clinical apparatus 42 that is associated with the auxiliary conveyor 32. Protraction of the divert head 196 will block off the main transport lane 60 and direct the sample tube 106 onto the sidebar lane 120 of the auxiliary conveyor 32.

If the label for the sample tube 106 at the divert gate 160 of the auxiliary conveyor 32 indicates that the sample tube 106 is not to be tested by the clinical apparatus associated with the auxiliary conveyor 32 the process control computer will cause the divert head 196 to be retracted. With the divert head 196 in a retracted position the sample tube 106 will continue to travel on the main transport lane 60 thereby bypassing the auxiliary conveyor 32 and the clinical apparatus 42.

Assuming the sample tube 106 is to be tested at the clinical apparatus 42 such sample tube 106 will be diverted onto the sidebar lane 120 which moves the sample tube 106 to the interface gate 170. The sample tube 106 is held in line at the interface gate 170 by the protracted finger 234 (FIG. 6) which holds sample tube 106 and other sample tubes 106 in line for singulation and label reading in a manner as previously described with respect to the interface gate 170 at the auxiliary conveyor 30. Label reading at the interface gate 170 is used to confirm that the sample tube 106 is to be tested by the clinical test apparatus 42.

Once the confirmatory reading has been taken at the interface gate 170 of the auxiliary conveyor 32, a robot (not shown) will remove the sample tube 106 from its singulation position for transfer to the clinical test apparatus 42. The unloaded puck 102 remains on the auxiliary conveyor 132 due to the vertical confinement provided by the ledges 136 and 138 (FIG. 4) at the conveyor edge portions 128 and 130. The plunger device 222 (FIG. 6) is then activated to retract the finger 234 and permit the unloaded puck 102 to travel to the next protracted finger 236 where it is held back by the finger 236 at the next puck rotating mechanism 244. The unloaded puck 102 is then reloaded with a sample tube 106 that has already been tested at the clinical test apparatus 42.

Figure 6:
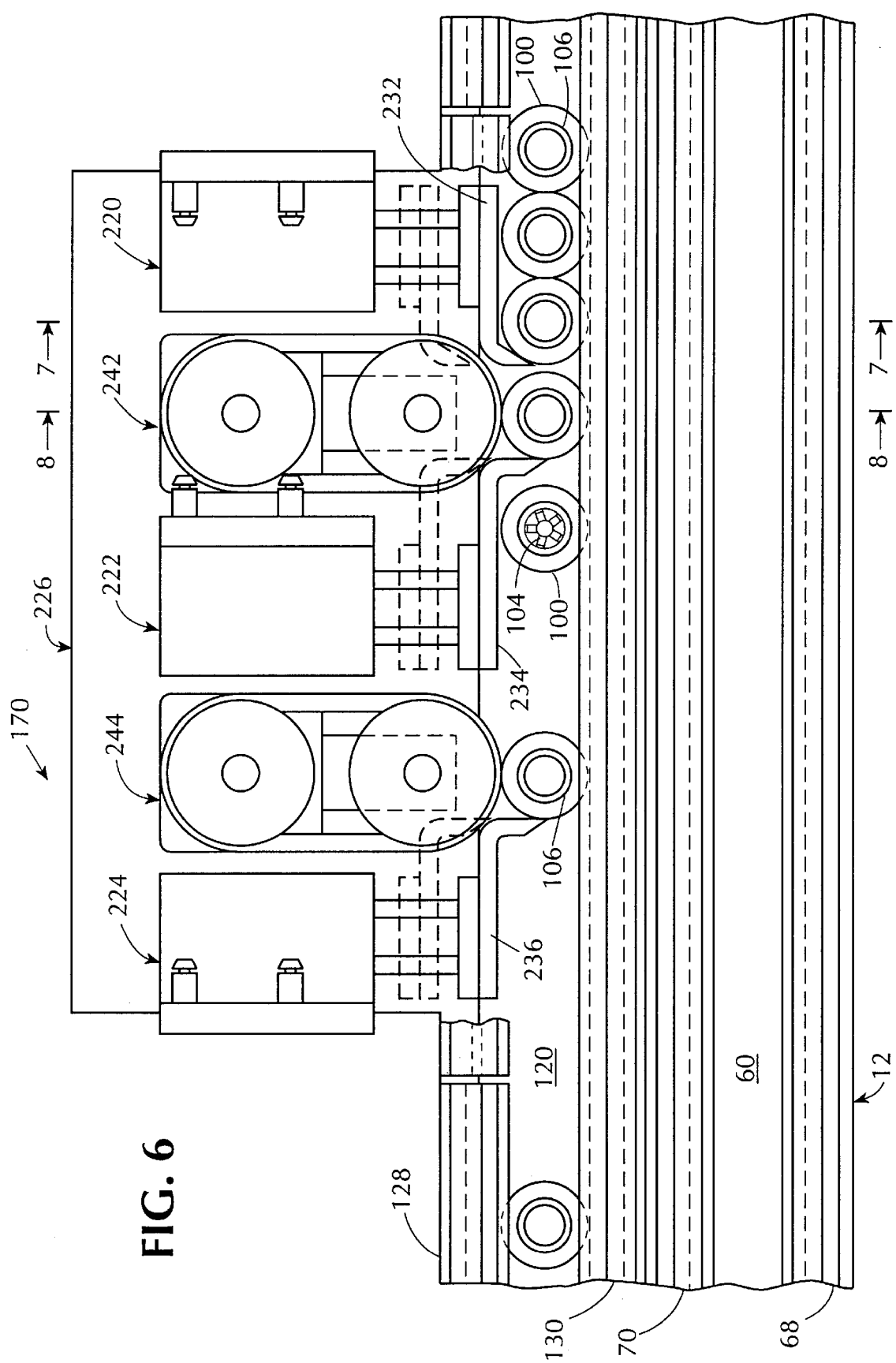
FIG. 6 is an enlarged schematic plan view of an interface gate device employed in the conveyor system.

It should be noted that the sample tube 106 that was robotically removed from the puck 100 at the singulator mechanism for transfer to the clinical test apparatus 42 is generally not the same sample tube 106 that is loaded in the empty puck 102 when the empty puck 102 is at the rotating mechanism 244 (FIG. 6). The unloading of the sample tube 106 from a puck 100 and the reloading of the puck 100 with a different sample tube 106 is due to the clinical test apparatus 42 being operated in continuous fashion.

Thus the clinical test apparatus 42 receives input sample tubes 106 to be tested simultaneously as it delivers output sample tubes 106 that have been tested. The label of the sample tube 106 that is at the puck rotating mechanism 244 is read by the label reader device at the puck rotating mechanism 244 and provides information to the process computer that the sample tube 106 has been tested at the clinical test apparatus 42. The plunger device 224 (FIG. 6) is then activated to retract the finger 236 and permit the sidebar lane 120 of the auxiliary conveyor 32 to move the sample tube 106 through the exit opening 148 of the interface gate 170 onto the main transport lane 60 in the direction of the clinical test apparatus.

The main transport lane 60 will carry the sample tube 106 to the next intersection that is governed by the next divert gate 160, namely the auxiliary conveyor 34 (FIG. 1) that is associated with the clinical test apparatus 44. Depending upon the information on the label 108 of the sample tube 106 and the information stored in the process control computer memory, the sample tube 106 will be either diverted onto the auxiliary conveyor 34 or allowed to stay on the main transport lane 60. If the sample tube 106 does not require any further testing it will not be diverted to any other auxiliary conveyors associated with clinical test apparatus and will usually be diverted to the auxiliary conveyor 30 for unloading at the unload station 40.

Each of the auxiliary conveyors 30–39 are powered by separate and independent motor devices. Thus the inclusion of additional auxiliary conveyors into the conveyor system 10 can be easily accomplished since the adjacent edge walls 70 and 130 of the main conveyor and the auxiliary conveyor can be detachably fastened together in any suitable known manner. Furthermore, the extrusions which form the edge walls 68, 70, 128 and 130 can be formed in standard sizes with and without the exit and entrance openings 146 and 148 to facilitate the addition of any other auxiliary conveyors.

If desired, auxiliary conveyors can be provided not only for transfer of tubes to clinical test apparatus but also for transfer of tubes to stations that perform other functions that may be considered beneficial for the processing of the sample tubes. For example, the next sequential station 42 from the load and unload station 40 rather than being associated with a clinical test apparatus can be used as a label check station for the purpose of checking whether a sample tube label 108 has a proper bar code, whether the label 108 has been properly affixed to the sample tube 106 and whether any other identification function is lacking in connection with the sample tube. The label check station will operate to remove any questionable sample tubes 106 from the conveyor system for remediation or disposal. The label check station will also operate to confirm that a sample tube has been properly labeled, and upon such confirmation the sample tube will be returned to the main transport lane 60.

Figure 23:
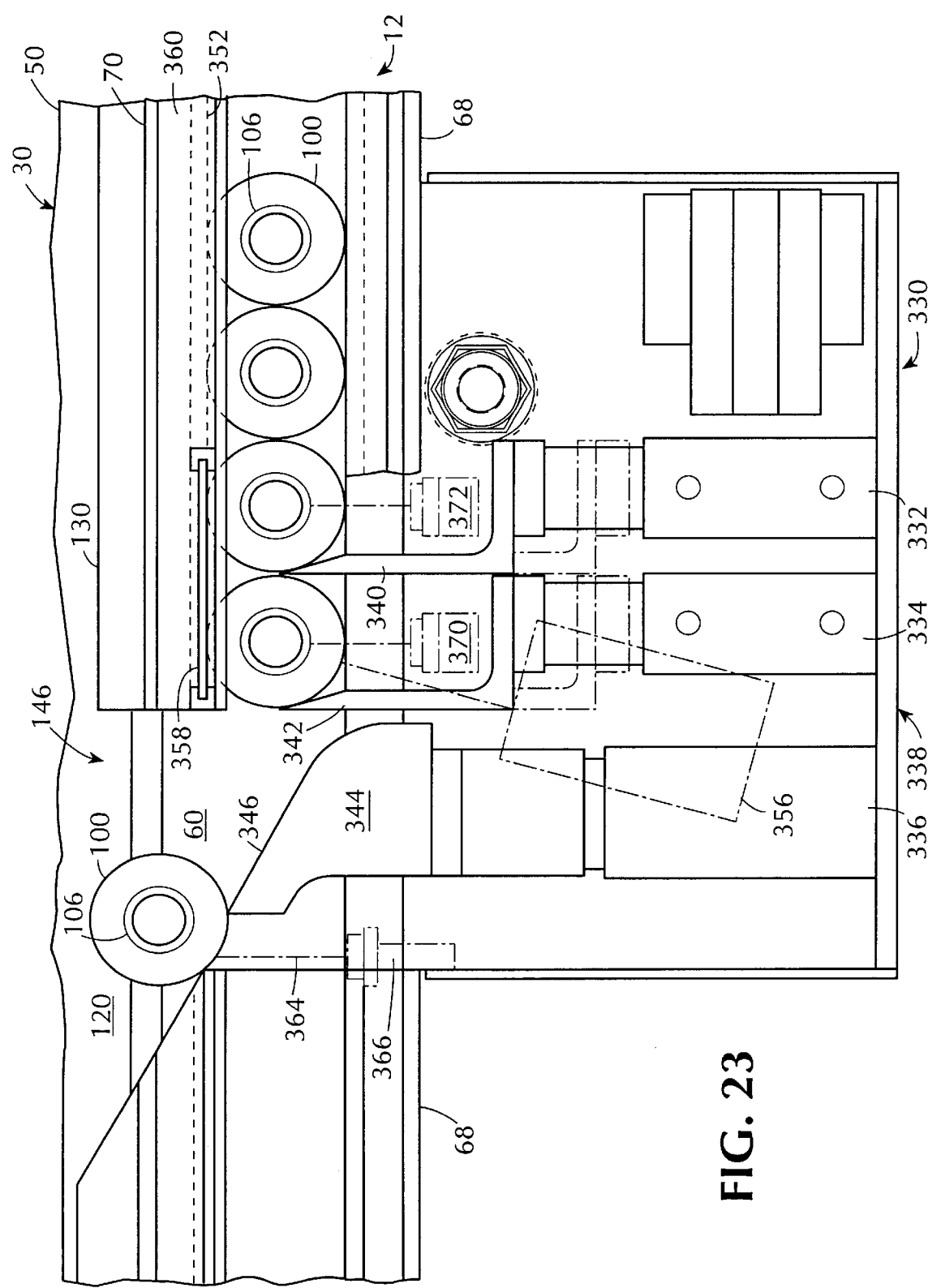
FIG. 23 is an enlarged schematic plan view of a divert gate incorporating a further embodiment of the invention; and, FIG. 24 is a side elevation thereof, partly shown in section.

Another embodiment of a divert gate is generally indicated by the reference number 330 in FIG. 23. The divert gate 330 is provided at the edge wall 68 of the transport conveyor 12 in substantial alignment with the sidebar entrance opening 146 at the upstream end 50 of the auxiliary conveyor 30. The divert gate 330 (FIG. 23) includes three pneumatically controlled plunger devices 332, 334 and 336 of known construction supported on a gate housing 338. The plunger devices 332 and 334 respectively include retractable fingers 340 and 342, and the plunger device 336 includes a retractable divert head 344 with an inclined surface 346.

Figure 24:
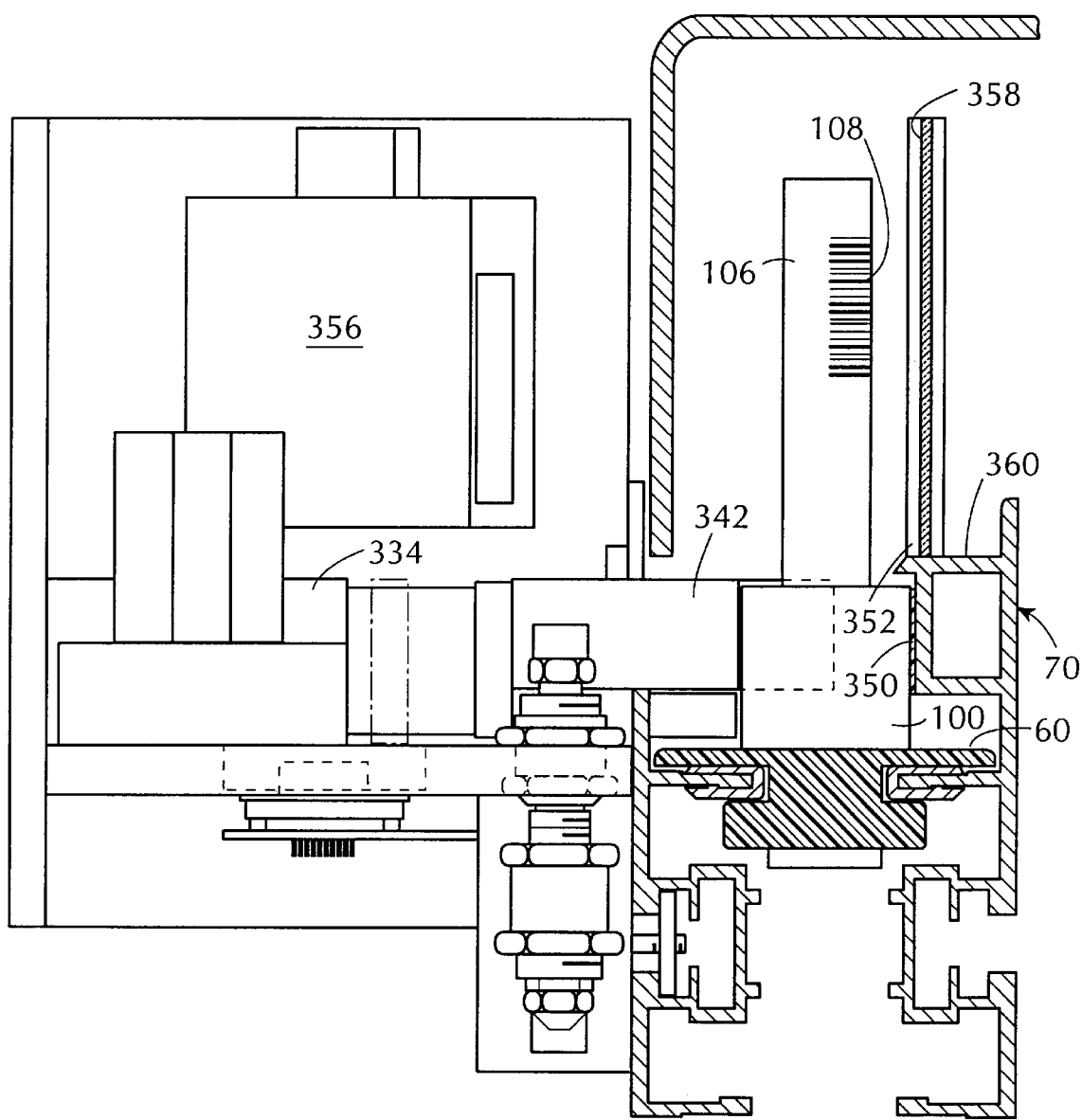

Referring to FIG. 24 a strip of tape 350 is secured to an inside surface 352 of the edge wall 70 directly across from the plunger devices 332 and 334. The tape 350 constitutes a contact surface that makes slight contact with the periphery of the pucks 100 when the pucks are directly across from the plunger devices 332 and 334. The movement of the conveyor belt 60 along with the slight touching of the tape 350 against the periphery of the pucks 100 causes a slight rotation of the pucks 100 as they move on the conveyor belt 60 past the tape 350.

A known label scanner or reader device 356 (FIG. 23) reads the bar code label 108 of a puck 100 that is held in position between the protracted fingers 340 and 342. A mirror 358 (FIGS. 23 and 24) is supported on a horizontal surface 360 of the edge wall 70 across from the plunger devices 332 and 334. The mirror 358 is positioned to reflect the bar code 108 of the sample tubes 106 when the bar code 108 is positioned in front of the mirror 358. Under this arrangement a bar code reading of the sample tube 106 can be obtained by the label scanner device 356 when the bar code label 108 faces the scanner device 356 or when the bar code label 108 faces the mirror 358. The slight rotation of the puck 100 by contact with the tape 350 facilitates reading of the bar code label 108 by the reader device 356. Thus the divert gate 330 does not require the puck rotating mechanism 190 of the divert gate 160.

If the bar code label 108 is oriented in a position that does not permit the scanner device 356 to obtain a reading of the bar code label 108, then the puck 100 will not be diverted to the side bar lane 120 and will remain on the main transport lane 60. However based on past performance there is a 95% chance that the sample tube 106 will have an orientation that permits the reader device 356 to obtain a reading of the bar code label 108.

When the respective fingers 340 and 342 of the plunger devices 332 and 334 are in a protracted position, the combination of the plunger devices 332 and 334 constitute a singulator device that enables the label reader device 356 to read the bar code label 108 of one sample tube at a time. The retractable fingers 340 and 342 are spaced apart a distance slightly larger than the puck diameter to permit the puck to rotate slightly between the protracted fingers 340 and 342 as previously described.

When the retractable finger 340 is in a protracted position as shown in FIG. 23 it retains the queue of pucks 100. Thus after a puck 100 has been singulated between the fingers 340 and 342 the puck label is read and the finger 342 can be retracted to release the singulated puck. If the bar code information indicates that the singulated puck should be diverted from the main transport lane 60 to the sidebar lane 120 the divert head 344 will remain in a protracted position to divert the singulated puck 100 in the manner shown in FIG. 23. If the bar code label information on the singulated puck 100 indicates that the puck 100 should remain on the main transport lane 60 the divert head 344 will be retracted to enable the singulated puck 100 to continue being moved on the main transport lane 60.

Regardless of whether the singulated puck 100 is or is not diverted from the main transport lane 60 to the sidebar lane 120 the puck 100 will pass across a beam 364 (FIG. 23) of a sensor 366. The sensor 366 upon sensing the puck 100 will signal the control means (not shown) of the conveyor system 10 to activate the plunger 334 to protract the finger 342 as shown in FIG. 23 for singulation of another puck 100 in the queue of pucks held back by the finger 340. The plunger device 332 will thus be activated to retract the finger 340 to enable the leading puck 100 in the queue of pucks that are held back by the finger 340 to move into engagement with the now protracted finger 342.

The sensor device 370 senses the presence of a puck 100 that has progressed to the finger 342 and signals the control means to activate the plunger device 332 to protract the finger 340 thereby singulating the progressive puck 100 between the protracted fingers 340 and 342. Another sensor device 372, in alignment with the plunger device 332 senses the presence of a puck 100 upstream of the protracted finger 340 to recognize that the sensed puck is being held back by the protracted finger 340.

Figure 20:
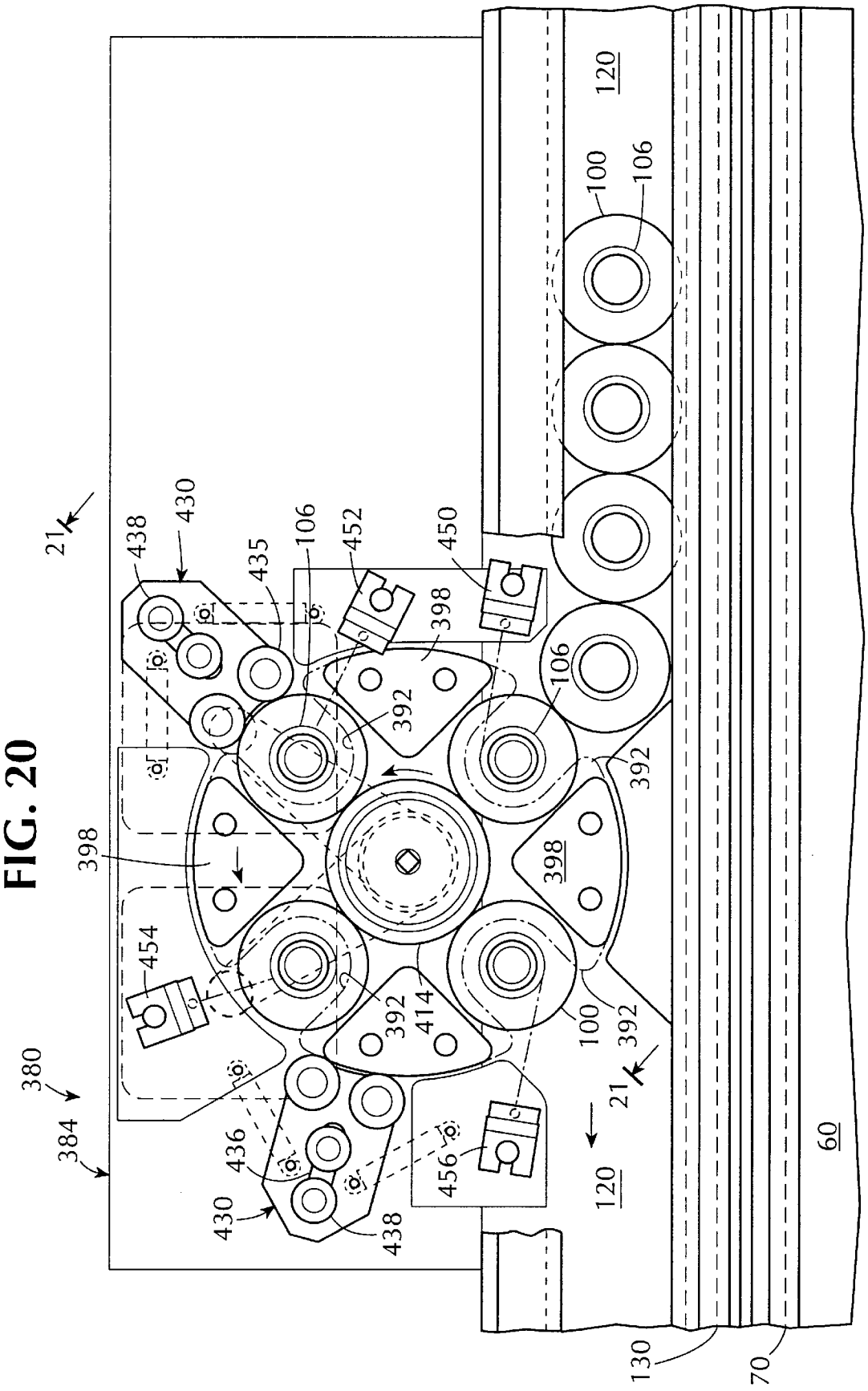
FIG. 20 is an enlarged schematic plan view of an interface gate incorporating another embodiment of the invention.
Figure 21:
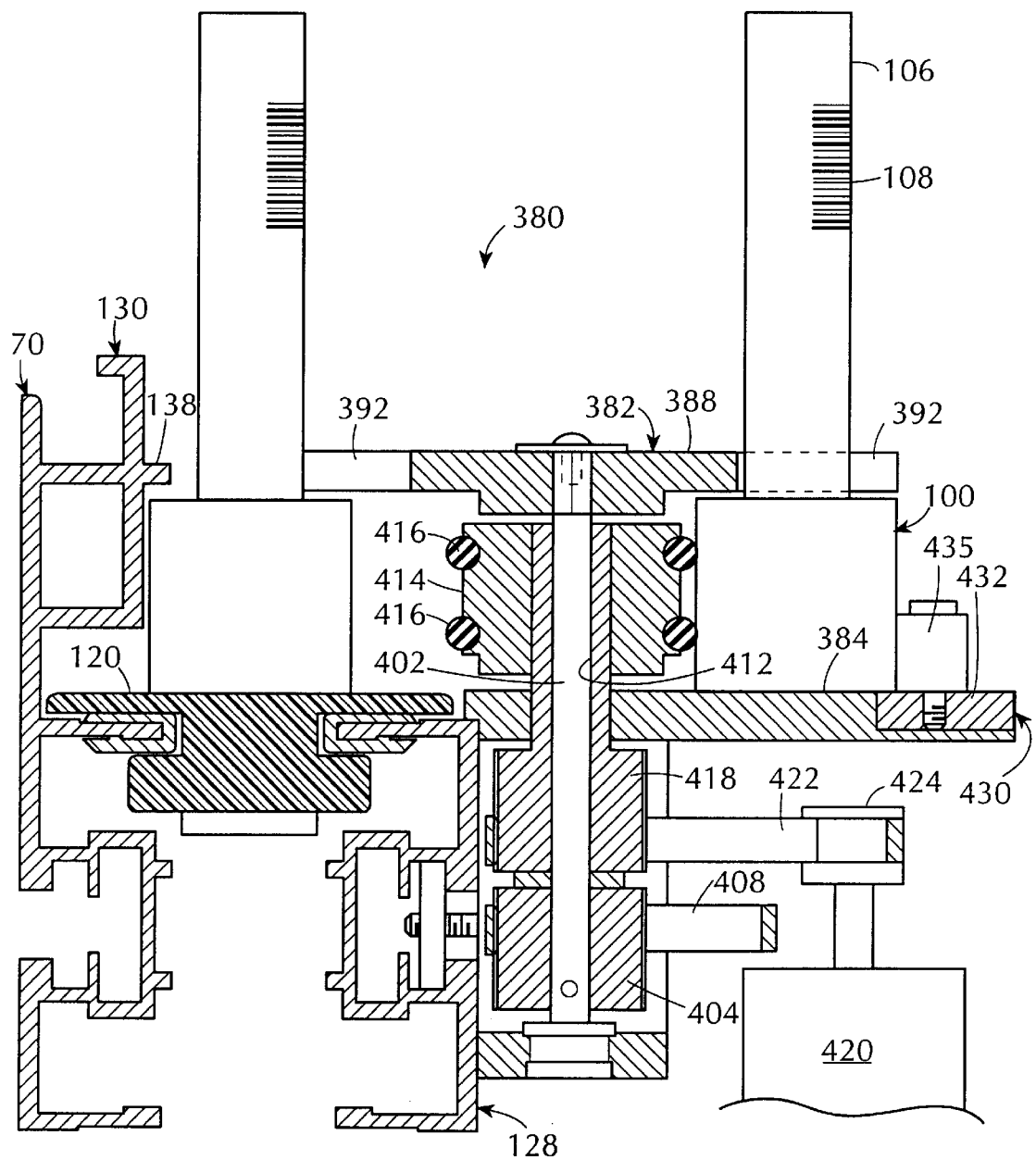
FIG. 21 is a sectional view thereof taken on the line 21—21 of FIG. 20.
Figure 22:
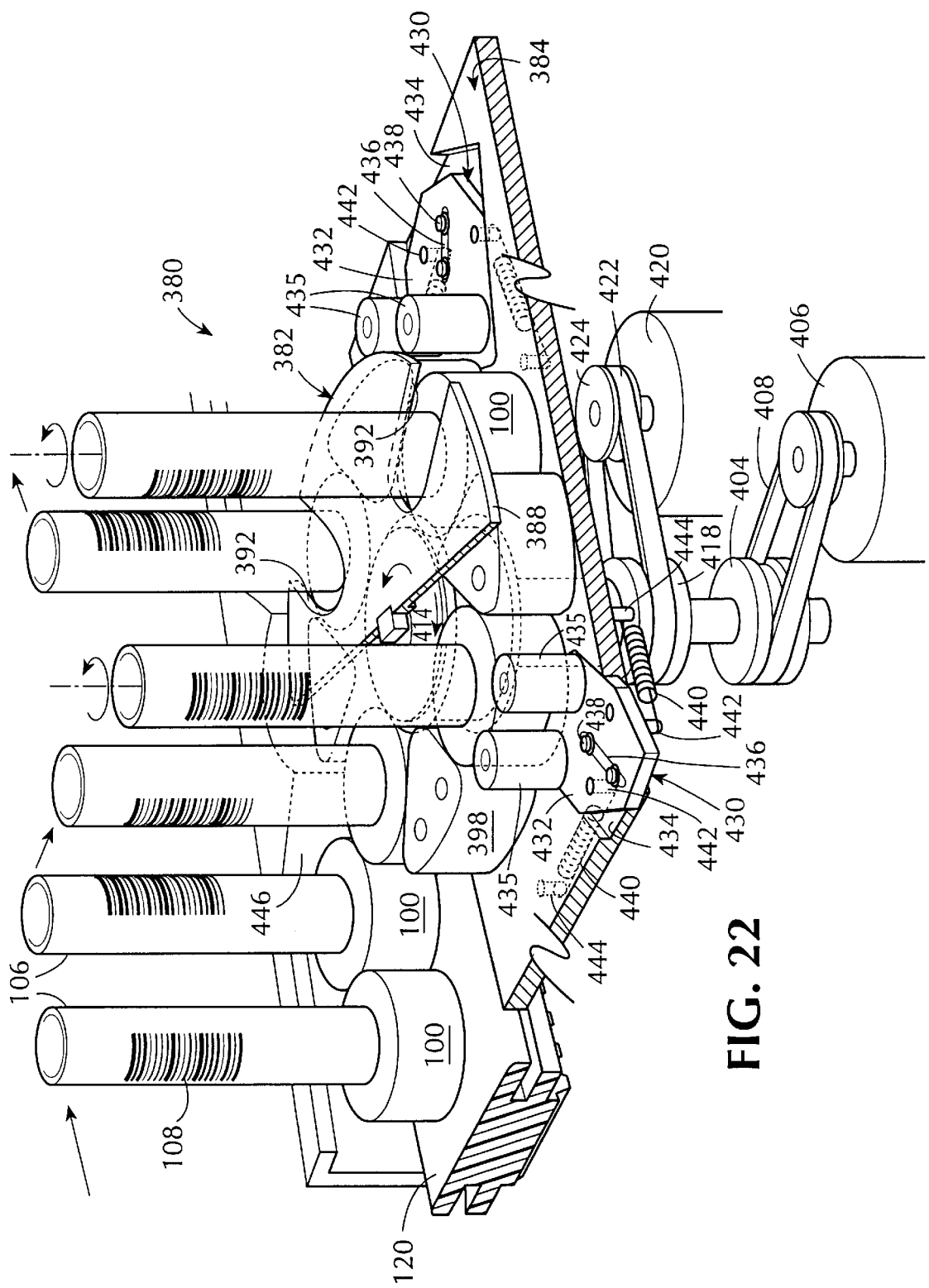
FIG. 22 is a perspective view thereof.

Another embodiment of the interface gate is generally indicated by the reference number 380 in FIGS. 20–22. The interface gate 380 includes a star wheel device 382 (FIG. 22) rotatable on a fixed support plate 384. The support plate 384 constitutes a portion of the gate housing for the interface gate 380 that is joined to the edge wall 128 (FIG. 21) of the sidebar conveyor belt 120.

The star wheel device 382 (FIG. 21) includes an upper rotatable plate 388 having four radially spaced sample tube recesses 392 shown in phantom outline in FIG. 20. The sample tube recesses 392 are wider than the sample tubes 106 and do not contact any portion of the sample tubes 106. The recesses 392 are also narrower than the outside diameter of the pucks 100, as most clearly shown in FIG. 20 to prevent the puck from elevating above the recesses 392 when a sample tube 106 is withdrawn from a puck 100.

Four generally triangular segments 398 are each secured to the upper rotatable plate 388 such that one of the segments 398 is provided between any two consecutive sample tube recesses 392. The segments 398 have a vertical thickness that is slightly less than the distance between the upper rotatable plate 388 and the fixed lower plate 384. The segments 398 are thus freely movable with the rotatable upper plate 388 relative to the fixed lower plate 384.

Referring to FIGS. 21 and 22 a shaft 402 has an upper end keyed to the center of the upper rotatable plate 388. An opposite lower end of the shaft 402 is keyed to a pulley 404 driven by a motor 406 (FIG. 22) via a belt 408. Thus the motor 406 rotates the upper plate 388 and the segments 398 in a counterclockwise direction as shown in FIG. 22.

Referring again to FIGS. 21 and 22 a puck rotating collar 414 with peripheral "O"-rings 416 is spaced between the upper plate 388 and the fixed lower support plate 384. A sleeve 412 concentric to the shaft 402 and freely rotatable relative to the shaft 402 has an upper end keyed to the puck rotating collar 414. A pulley 418 is formed at an opposite end of the sleeve 412 and is rotatable in a clockwise direction by a motor 420 via a belt 422 that passes around a motor pulley 424. The collar 414 is thus rotatable by the motor 420 between the upper plate 388 and the lower plate 384 in a clockwise direction as shown in FIG. 22.

A pair of biasing units 430 are provided on the fixed lower support plate 384 to bias the pucks 100 against the puck rotating collar 414 when the pucks 100 are guided past the biasing units 430 by the star wheel device 382. Each biasing unit 430 includes a plate 432, slidable in a recess 434 of the lower support plate 384. A pair of biasing rollers 435 are rotatably mounted on the support plate 384 to engage a surface portion of the pucks 100 that is opposite the puck rotating collar 414, to urge the pucks against the collar 414. The slide plate 432 has a guide slot 436 that receives spaced guide pins 438 fixed to the lower support plate 384 that permit the slide plate 432 to move toward the pucks 100 with a limited range of movement. A pair of biasing springs 440 are secured at one end to a post 442 on the slide plate 432 and at an opposite end to a post 444 on the support plate 384 to urge the slide plate 432 and the rollers 435 toward the pucks 100.

Referring to FIGS. 20 and 22 a deflector member 446 on the edge wall 130 of the side bar lane 120 deflects a puck 100 from the sidebar lane 120 into a tube recess 392 of the star wheel device 382.

A sensor 450 at the gate 380 (FIG. 20) senses that a sample tube 106 has entered the tube recess 392 at the 5 o'clock position of the star wheel device 382. The sensor signals the control means for the conveyor system 10 to actuate the motor 406 to rotate the star wheel device 382 and the entered puck 100 approximately 90 degrees to the 2 o'clock position of FIG. 20. The biasing unit 430 at the 2 o'clock position urges the entered puck 100 against the puck rotating collar 414 to rotate the sample tube 106 for bar code reading purposes.

A sensor 452 at the gate 380 senses the presence of the rotating sample tube 106 and signals the control means of the conveyor system 10 to cause the bar code reader device (not shown) to read the bar code of the rotating sample tube 106 in the 2 o'clock position. A robot (not shown) removes the sample tube from the puck in the 2 o'clock position and transfers such sample tube to an analysis system (not shown) for processing. Thus the puck at the 2 o'clock position of the star wheel device 382 in FIG. 20 is emptied of its sample tube. The sensor 452 senses the removal of the sample tube from the puck 106 in the 2 o'clock position and signals the control means for the conveyor system 10 to cause the motor 406 to rotate the star wheel device 382 another 90 degree increment to the 11 o'clock position of FIG. 20.

A sensor 454 at the gate 380 senses that there is no sample tube in the puck 100 at the 11 o'clock position of FIG. 20. A robot (not shown) transfers a processed sample tube from the sample analysis system at the gate 380 (not shown) to the empty puck at the 11 o'clock position of FIG. 20. The sensor 454 at the gate 380 senses when the sample tube 106 has been placed in the puck 100 at the 11 o'clock position and signals the control means to actuate the motor 406 to rotate the star wheel device 382 approximately 30 degrees to move the puck 100 from the 10 o'clock position into alignment with the biasing unit 430 at the 9 o'clock position of FIG. 20. The biasing unit 430 at the 9 o'clock position urges the puck 100 against the puck rotating collar 414 to rotate the sample tube 106 to permit a bar code label reading of the sample tube 106 by a scanner (not shown).

After the bar code label of the puck 100 in the 9 o'clock position has been read by the scanner device, the control means actuates the motor 406 to rotate the star wheel device 382 to the 7 o'clock exit position as shown in FIG. 20. The puck 100 can thus exit the interface gate 380 at the 7 o'clock position to move onto the sidebar lane 120. Further rotation of the star wheel device 382 will not begin until the 7 o'clock position is empty. Thus a sensor device 456 at the gate 380 senses when the puck 100 has left the 7 o'clock exit position of the star wheel device 382.

Under this arrangement, each time the star wheel device 382 indexes 90 degrees an additional puck 100 can be diverted by the deflector member 446 into the 5 o'clock position of the star wheel device 382 as shown in FIG. 20 for pick-up of a sample tube from the diverted puck and replacement of another sample tube in the empty puck as previously described. It should also be noted that a puck entering the gate 380 can exit the gate 380 without removal of its sample tube 106 if the information read on the bar code label 108 indicates that the tube 106 is not to be processed by the analysis system at the gate 380.

Figure 16:
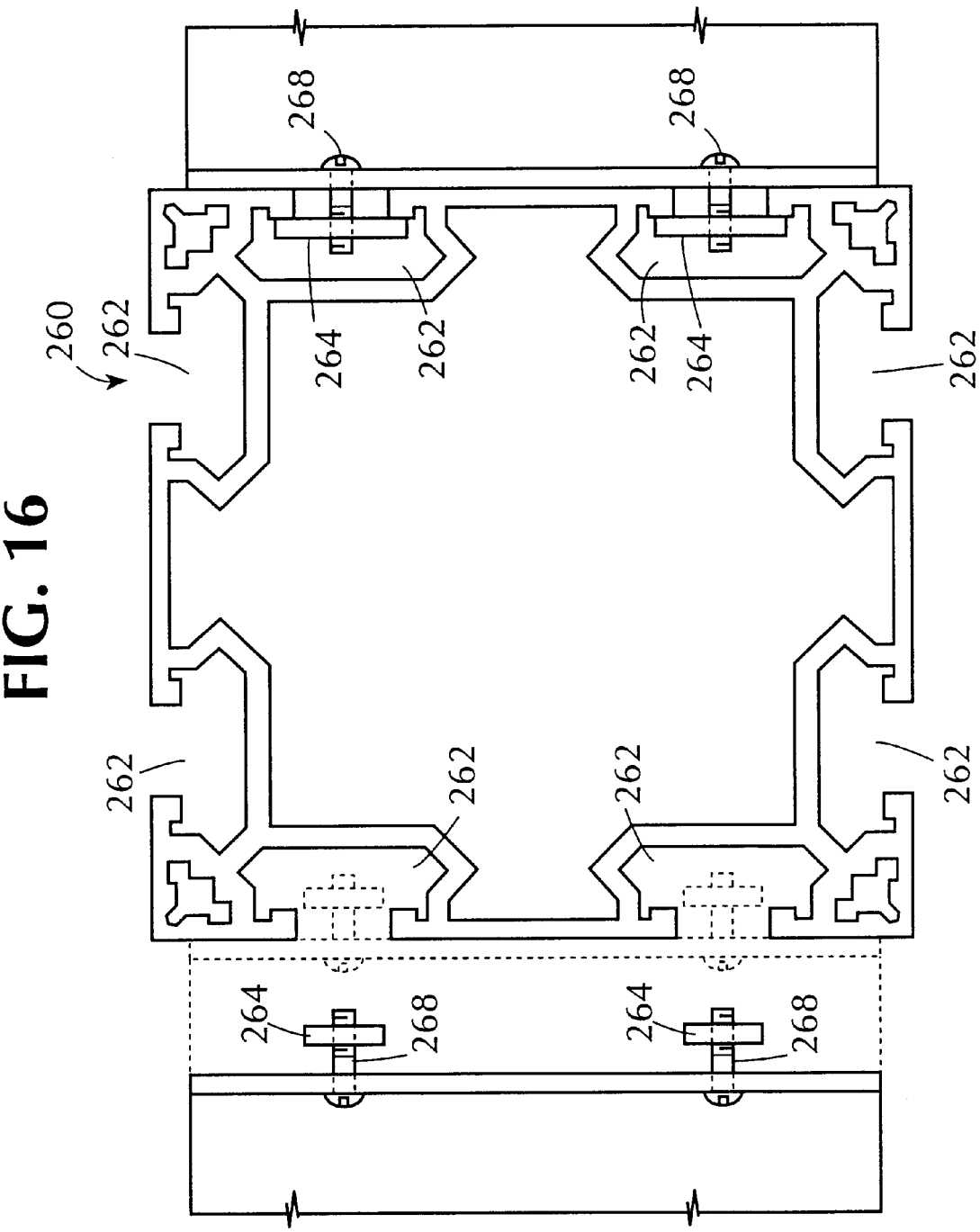
FIG. 16 is a top end view of a support column or stanchion of the utility support system.
Figure 17:
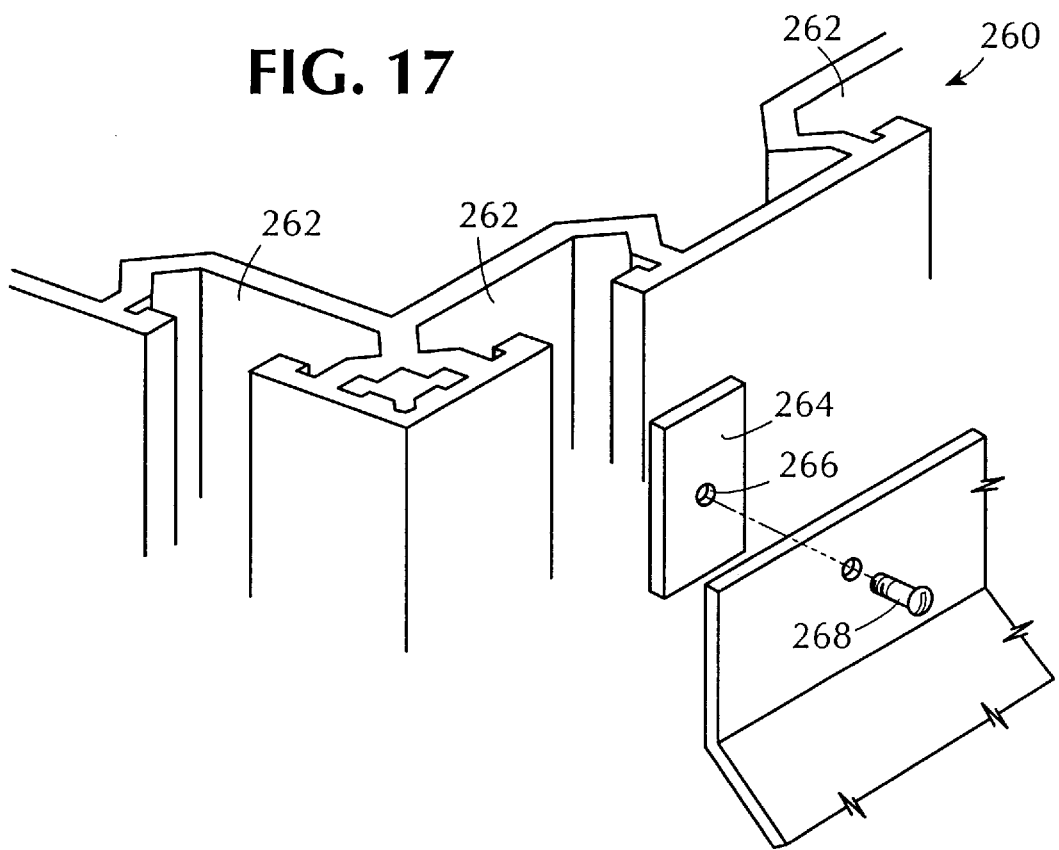
FIGS. 17 and 18 are fragmentary perspective views thereof showing adjustable securement members being joined to the support column to support the utility structure shown in FIG. 12.
Figure 18:
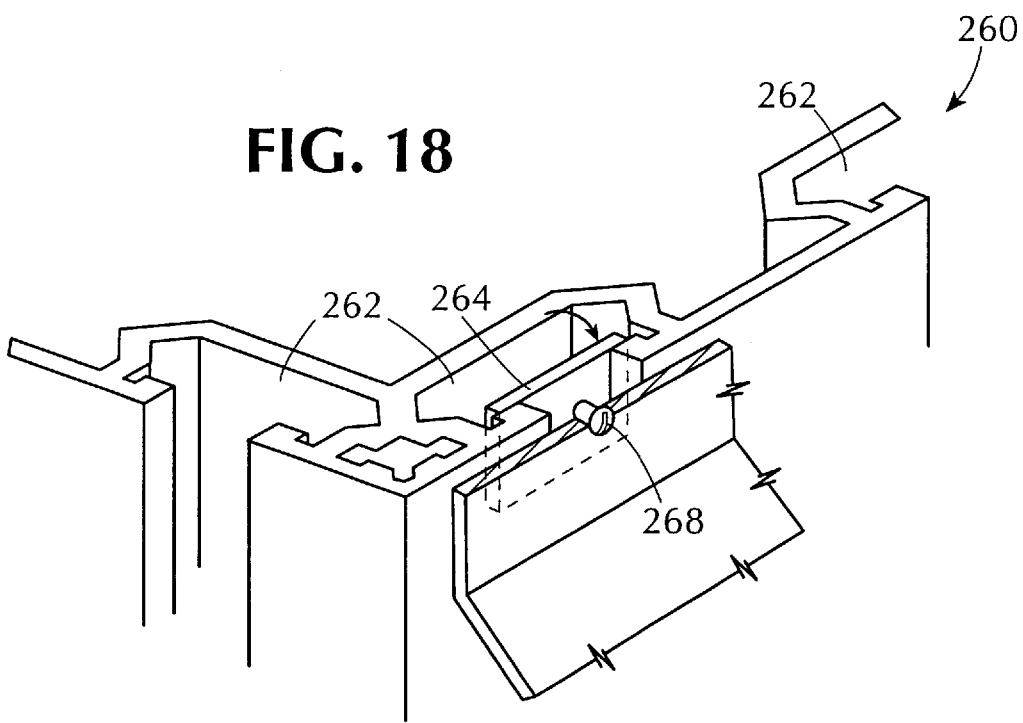
Figure 19:
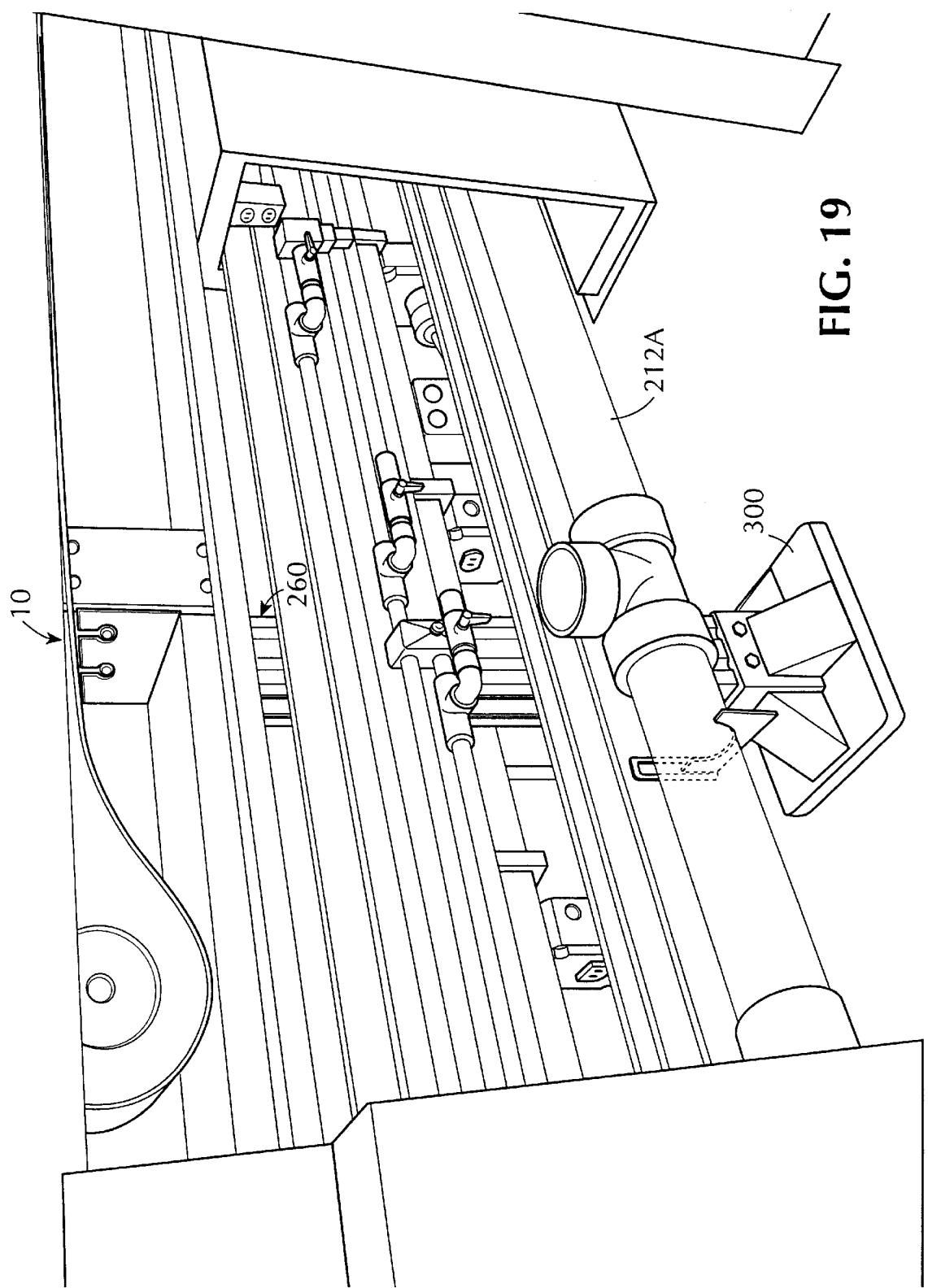
FIG. 19 is a pictorial view of the utility structure supported on the support columns.

The main transport conveyor 12 and the auxiliary conveyors 30–39 are commonly supported on identical column members 260 (FIGS. 9–12) that are spaced a predetermined distance from each other. The column members 260 are a known structure for supporting conveyors. As shown in FIGS. 16–18, the column member 260 includes vertical slots 262 that are open at a top end of the column. The slots 262 are engageable by a rectangular securement plate 264 having an opening 266 for a fastener 268.

The securement plate 264 can be installed in the vertical slot 262 at the top end of the column 260, or if desired, the plate 264 can be initially installed with the narrow side up in the slot 262. The securement plate 264 can then be rotated in a known manner to a locking orientation as shown in FIG. 18.

Bracket members 270 (FIG. 4) are provided near an upper end of each of the columns 260 to join the edge wall 68 of the conveyor 12 to the column 260. The adjacent edge walls 70 and 130 are integrally joined in any suitable known manner.

For example, although not shown, the fasteners 268 can be passed through the bracket members 270 (FIG. 4) to access one or more of the securement plates 264 in one or more of the vertical slots 262 of the column members 260.

Figure 8:
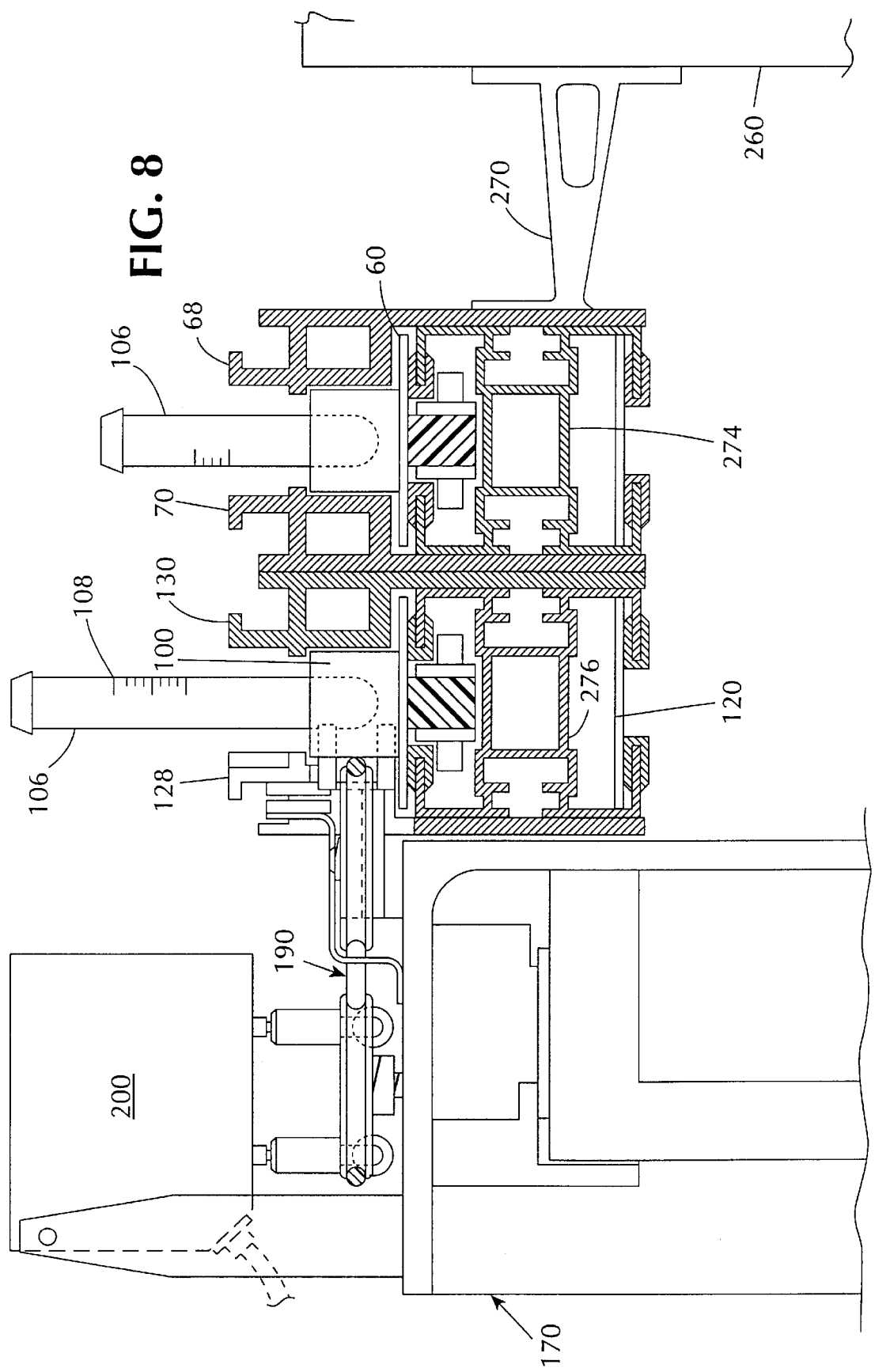
FIG. 8 is a sectional view taken on the line 8—8 of FIG. 6.
Figure 9:
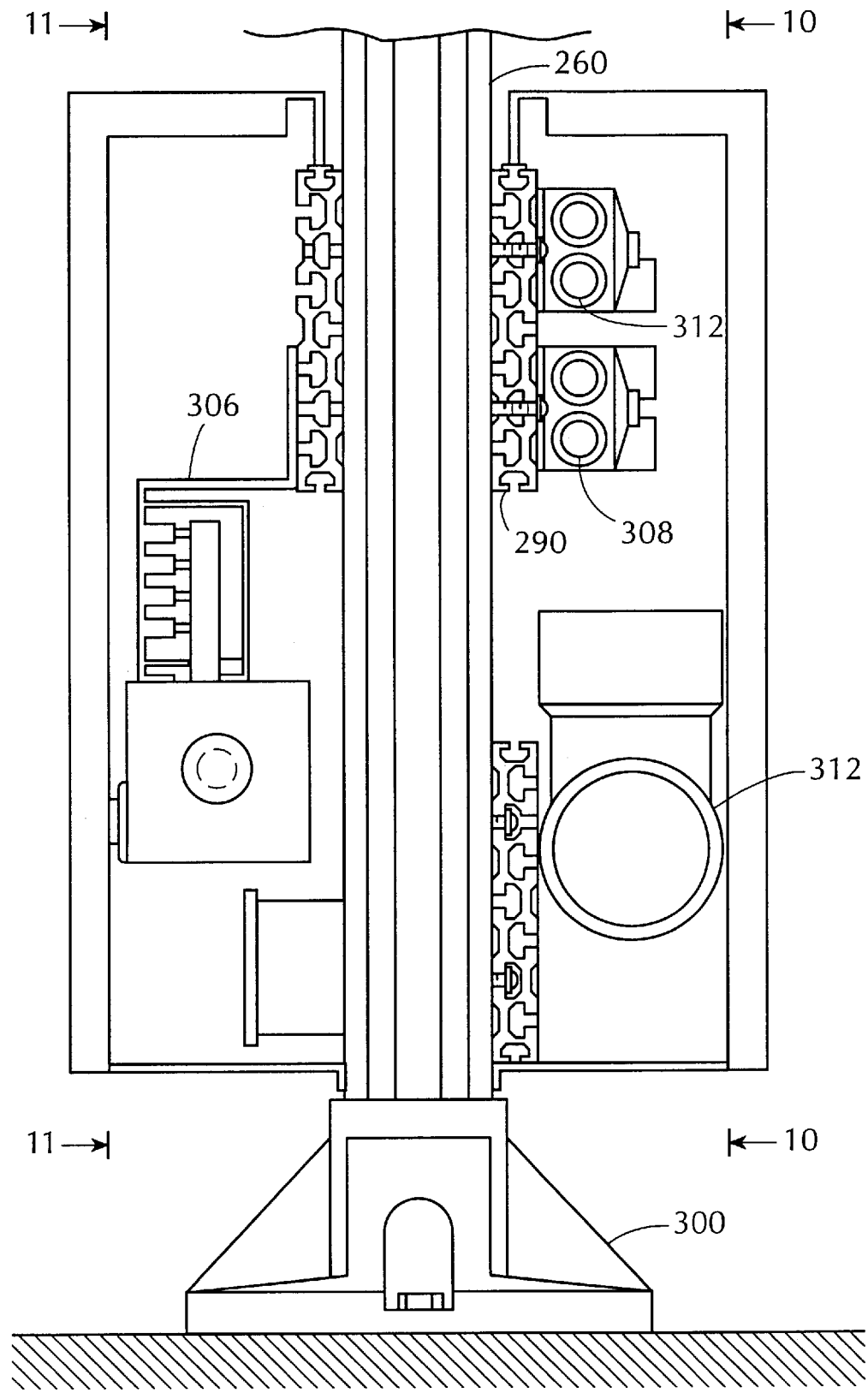
FIG. 9 is a fragmentary elevational view of the support structure for the conveyor system.
Figure 10:
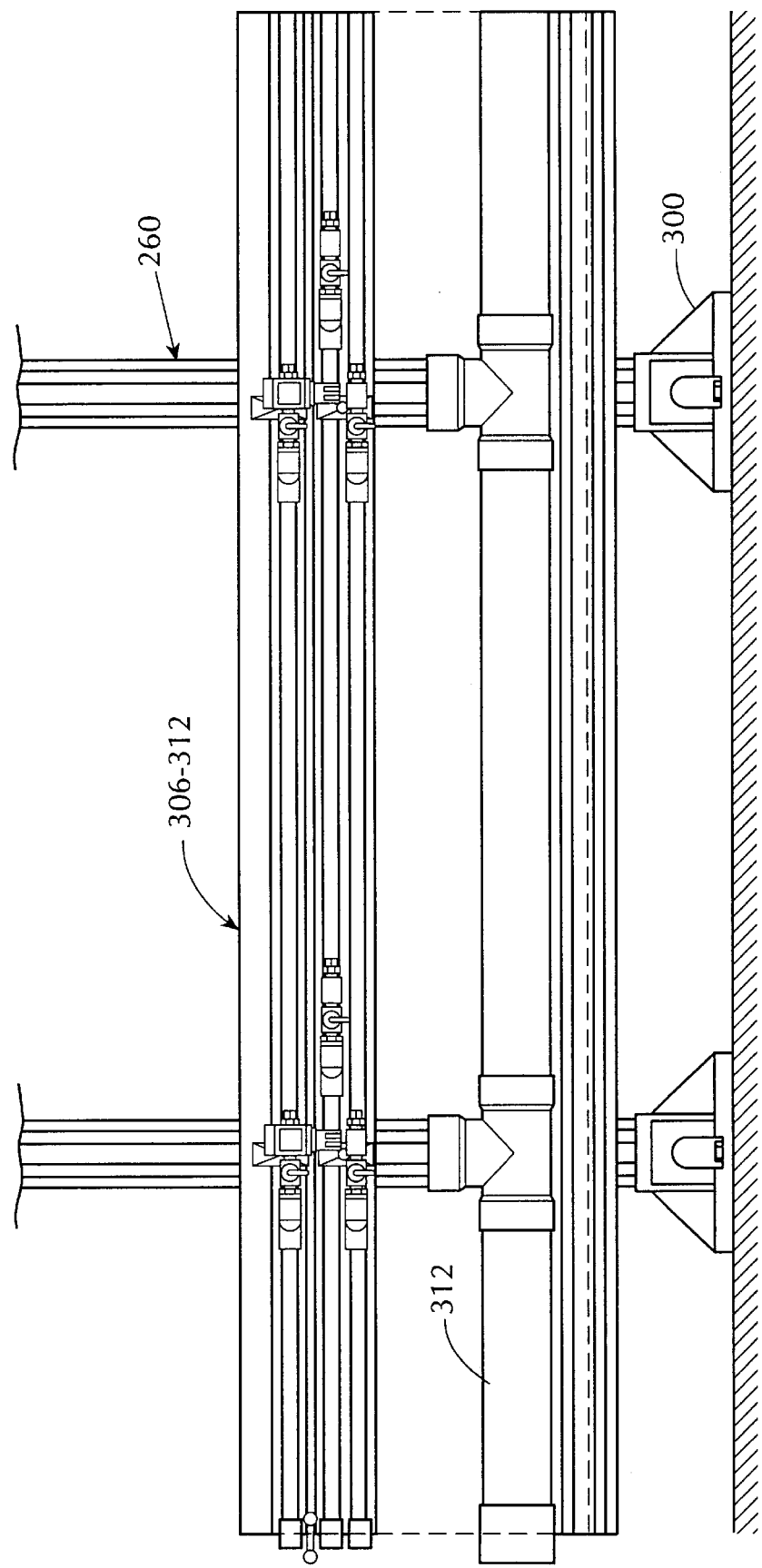
FIG. 10 is a sectional view taken on the line 10—10 of FIG. 9.
Figure 11:
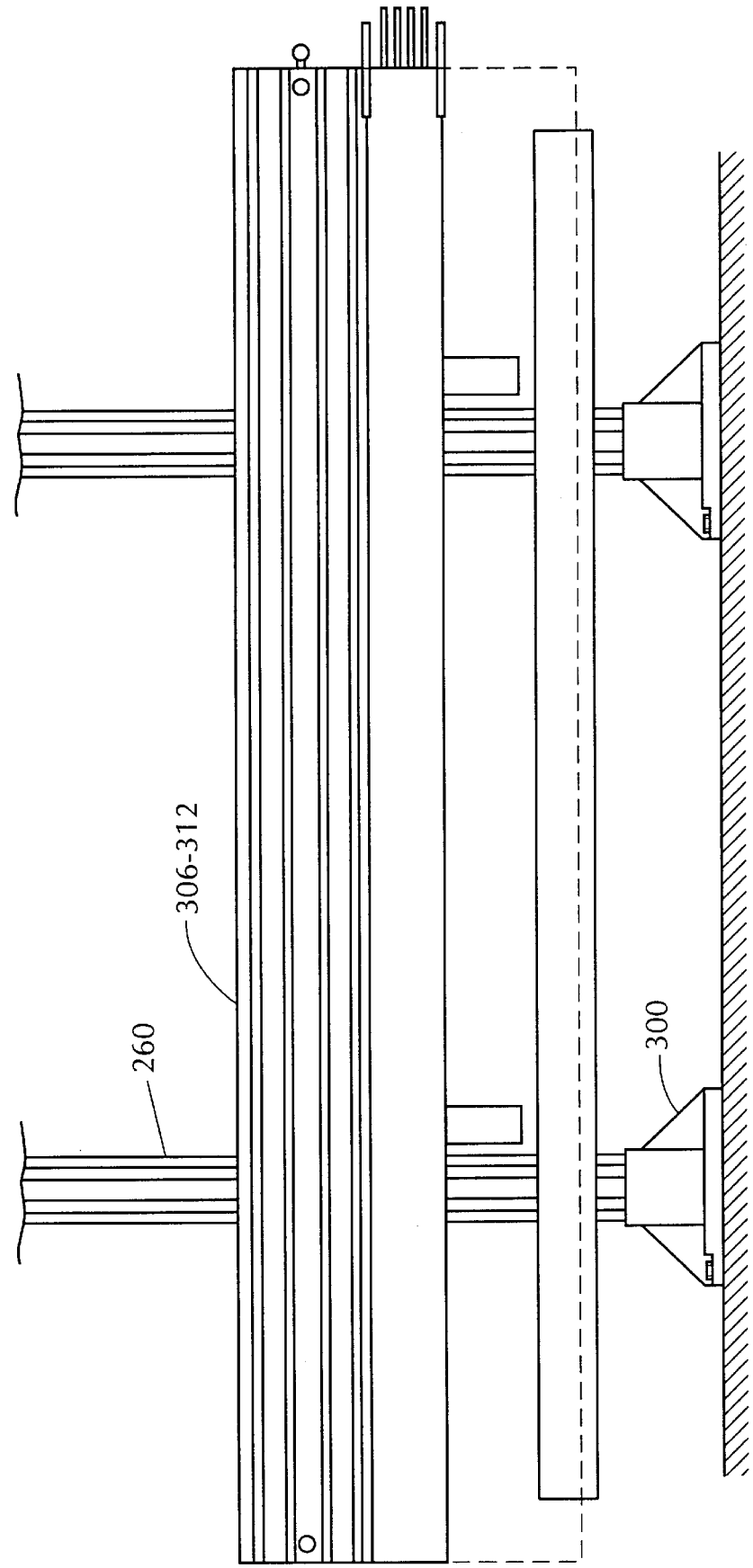
FIG. 11 is a sectional view taken on the line 11—11 of FIG. 9.
Figure 12:
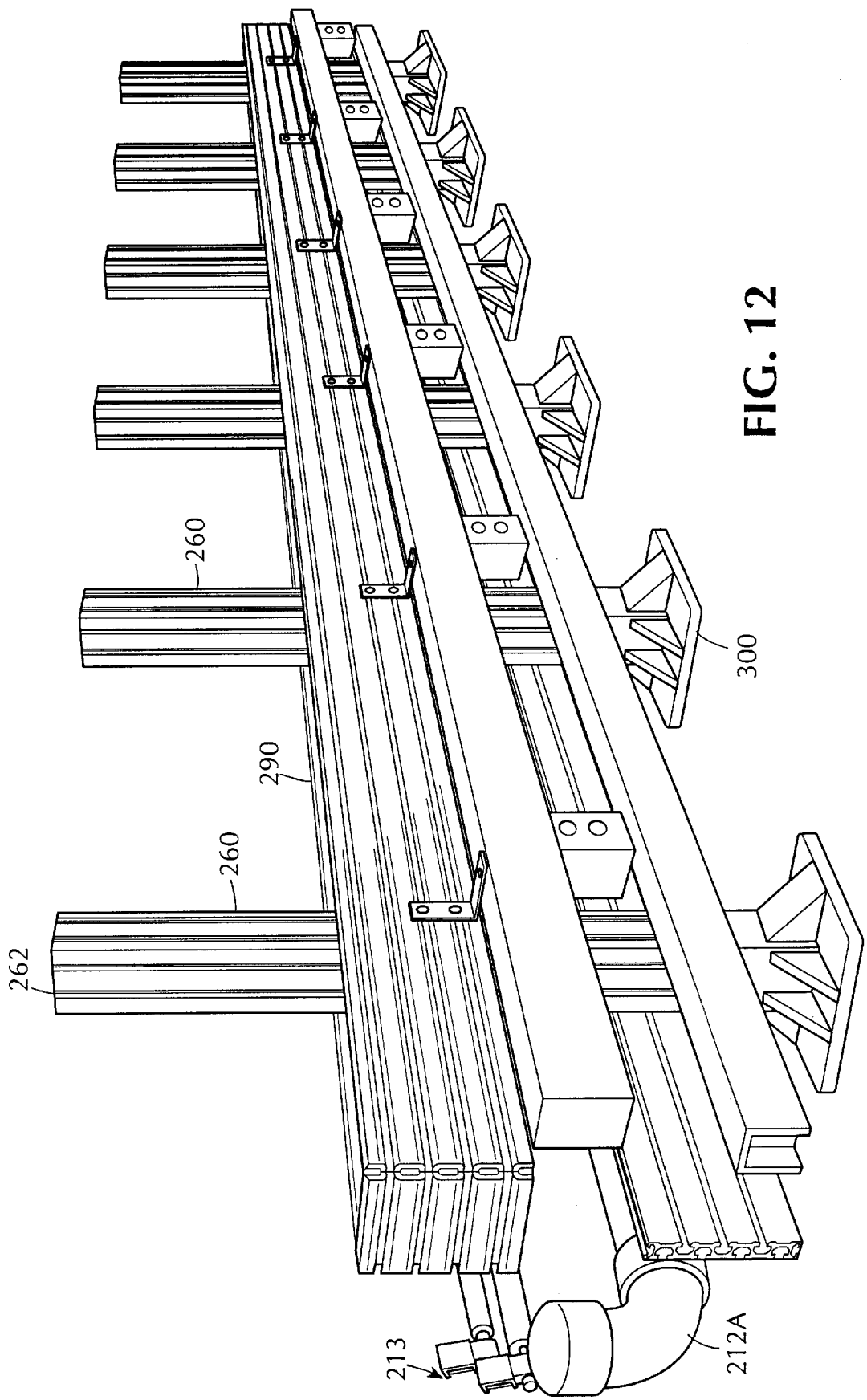
FIG. 12 is a perspective view of the utility support system of the conveyor incorporating a further embodiment of the invention.

In addition a joining member 274 (FIGS. 7 & 8), which supports the conveyor 12, joins the edge wall 68 to the edge wall 70. Another joining member 276, which supports the auxiliary conveyors 30–39, and is similar to the joining member 274, joins the edge wall 128 to the edge wall 130. Thus the bracket members 270 extending from the column members 260 support the conveyers 12 and 30–39 as well as the respective edge walls 68, 70, 128 and 130 in cantilever arrangement with respect to the column members 260.

It will be noted that the edge walls 68, 70, 128 and 130 as well as the bracket members 270 and the joining members 274 and 276 can each be formed as extrusions of predetermined length.

Figure 15:
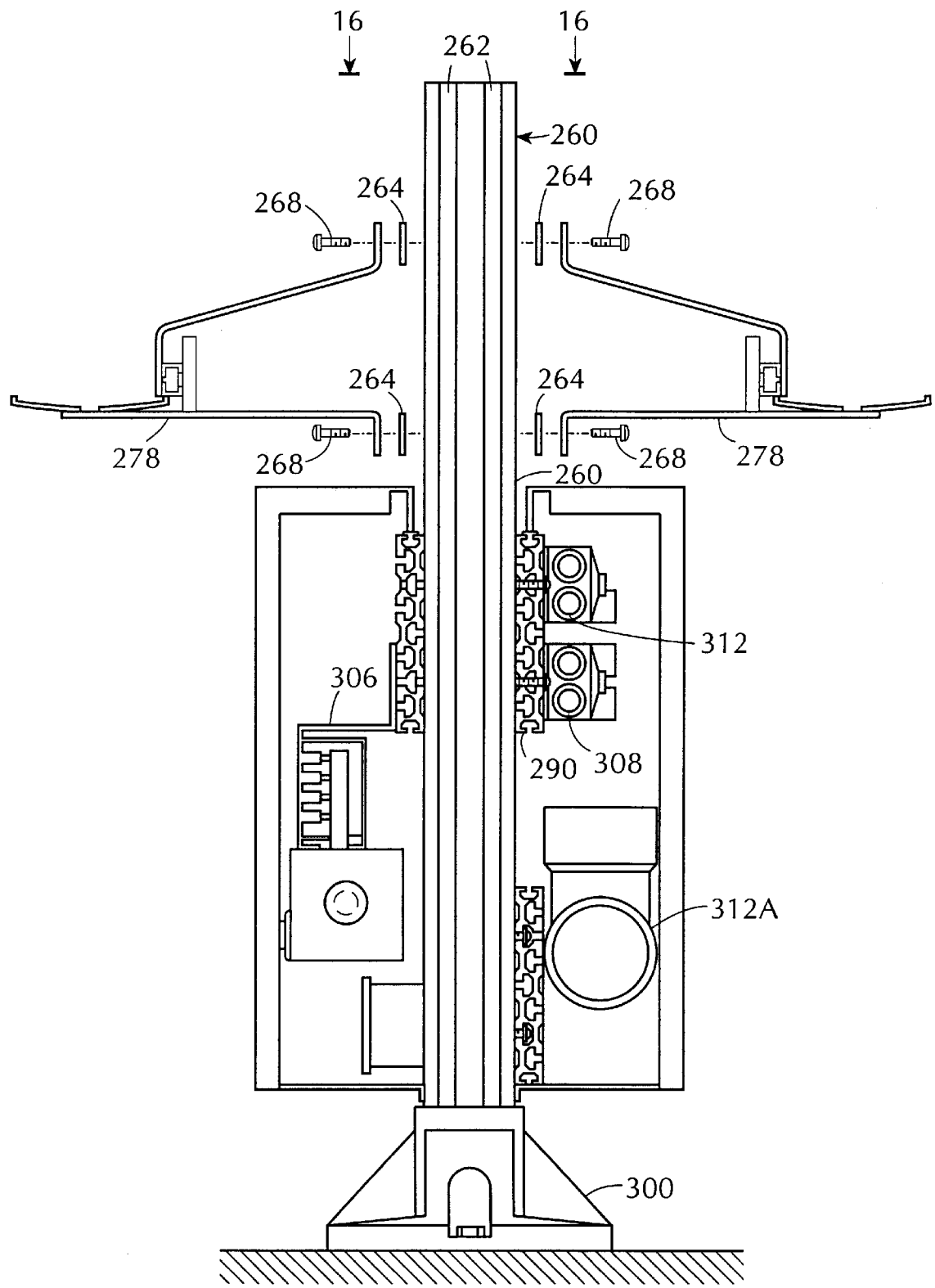
FIG. 15 is an opposite end view thereof, on a reduced scale, showing the utilities below a drip pan of the conveyor.

A drip pan 278 (FIGS. 4 & 15) for collecting any drippage from the conveyor can also be secured to the columns 260 below the conveyor. Thus, referring to FIG. 15, the securement plate 264 and the fastener are used in the manner previously described to secure the drip pan 278 to the column 260.

Figure 13:
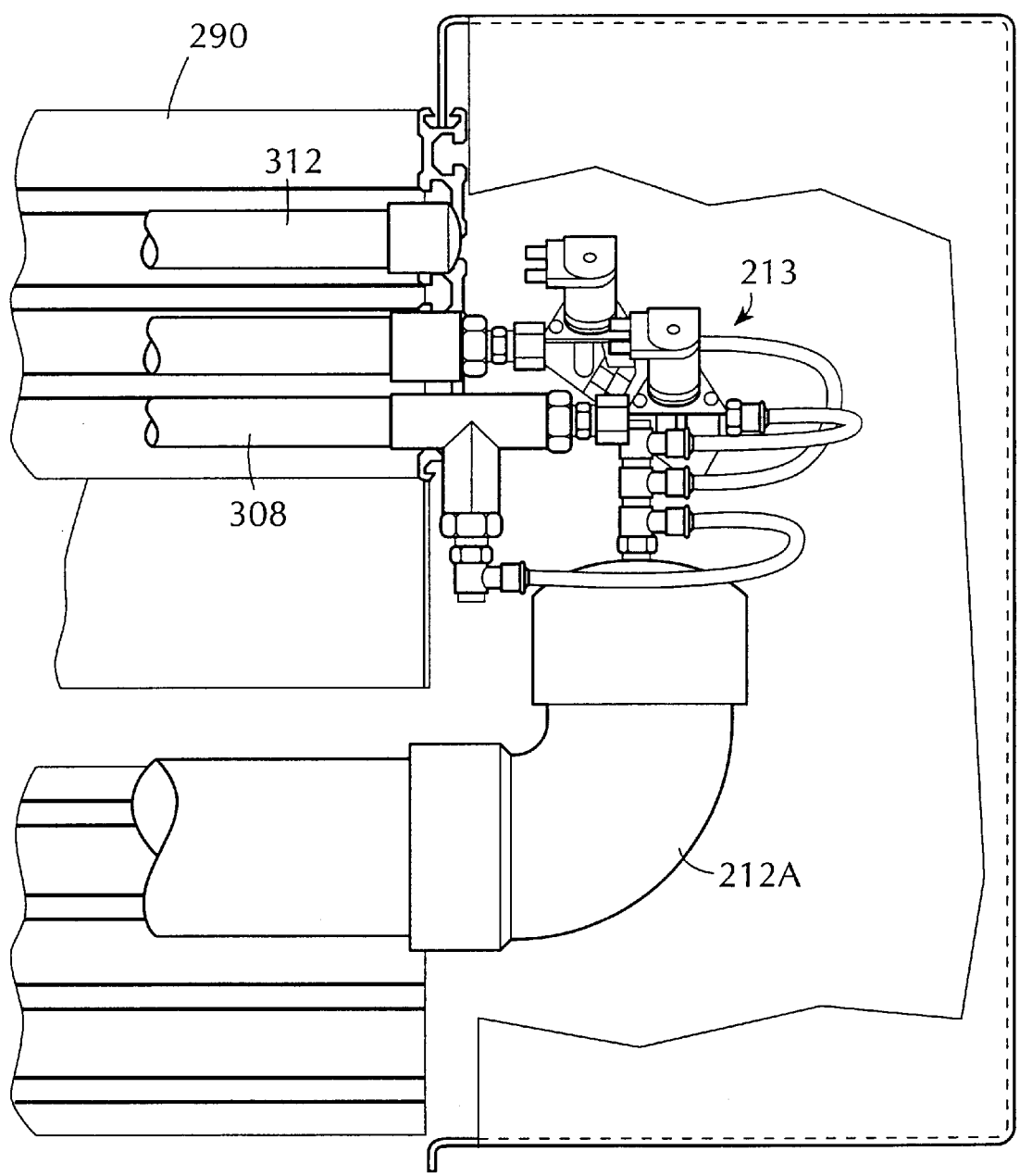
FIG. 13 is a fragmentary elevation view from the left side of FIG. 12.
Figure 14:
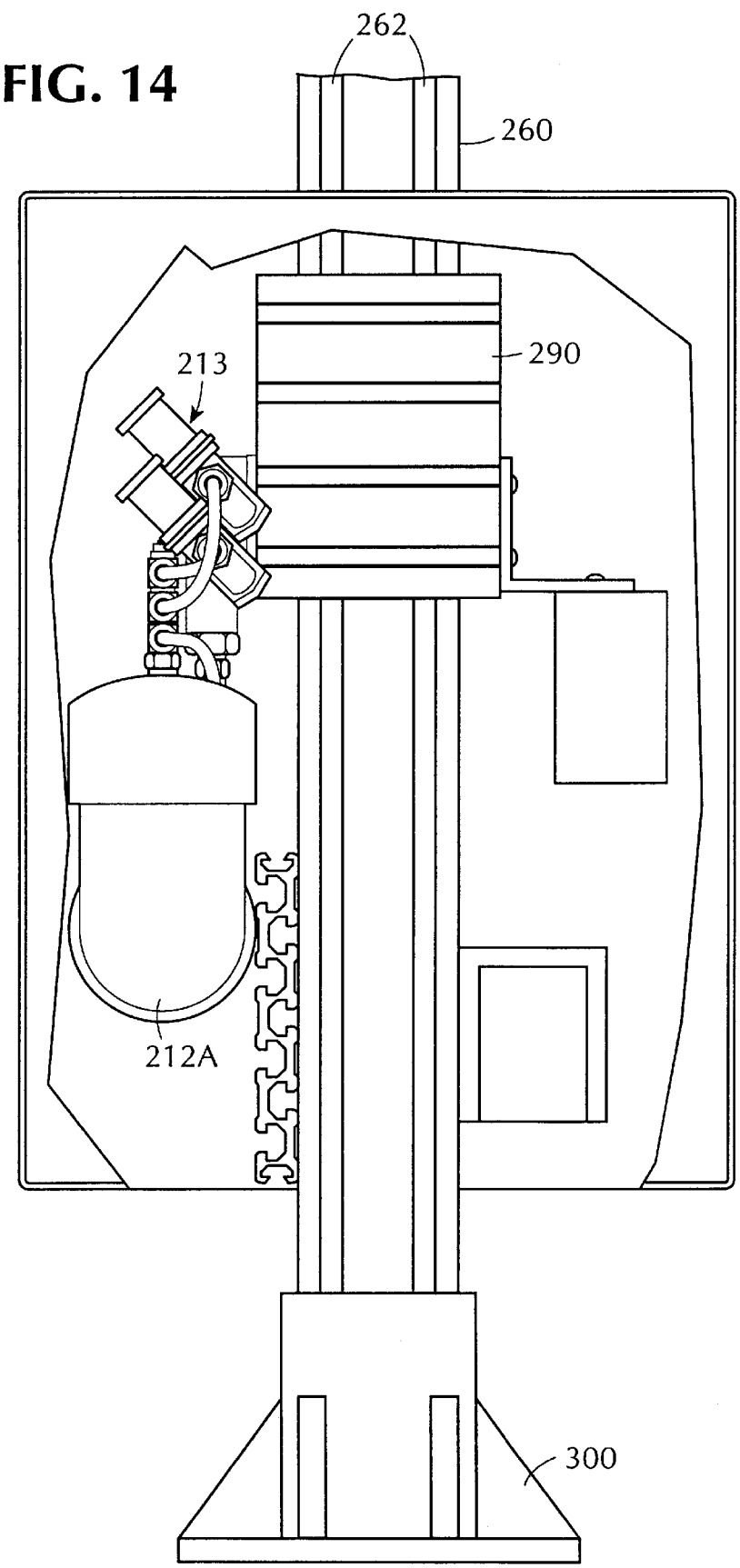
FIG. 14 is an end view thereof, showing the utilities in a cabinet, with portions of the cabinet broken away.
Figure 15A:
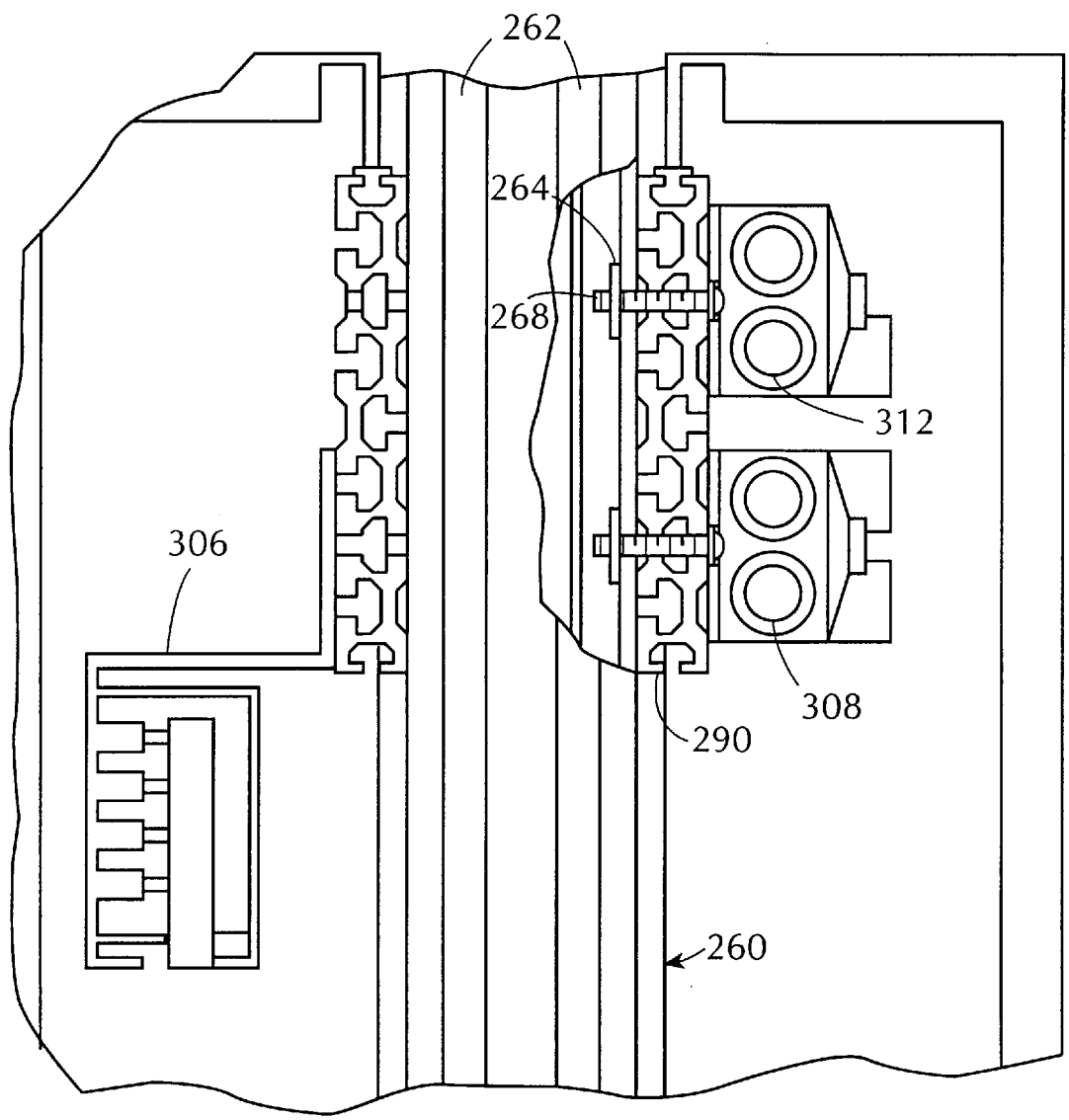
FIG. 15A is an enlarged fragmentary detail partly shown in section of the structure shown in FIG. 15.

Service support brackets 290 (FIGS. 9, 15 & 15A) are joined to the column members 260 between the bracket members 270 (FIG. 4) and a base portion 300 (FIGS. 9 and 15) of the column members 260, also using the securement plate 264 and the fasteners 268 to lock onto the column members 260. The service support brackets 290 (FIGS. 9, 15 and 15A) hold boxes 306 for electrical service, conduits 308 for air pressure and vacuum service and conduits 312, including a waste line 312A, for plumbing service to the conveyor system 10 and to any of the clinical test apparatus associated with the conveyor system 10. Any suitable known valving, switches and solenoid devices 313 (FIGS. 13 and 14) are provided on the conduits 306–312 to control the utility service to the conveyor system 10.

Under this arrangement all utilities which service the conveyor system 10 are carried by the support columns 260 of the conveyor system. No extraneous drops, cords or wires need be suspended over the conveyor or recessed in the ground below the conveyor. In addition much if not all of the cabinetry for the conveyor can be supported by the support system in the manner shown in FIGS. 3, 9, 14, 15, 15A & 19.

Some advantages of the invention evident from the foregoing description include a conveyor system having a main transport lane and a sidebar lane that are substantially parallel to each other and operate side-by-side, a novel conveyor system which includes a main transport conveyor that runs in an endless circuit and auxiliary conveyors provided alongside the main conveyor at the straight line paths of the main conveyor to permit crossover between the main conveyor and the auxiliary conveyor and vice versa, a novel conveyor system wherein the main conveyor and auxiliary conveyors are each powered by separate motors, a novel conveyor system wherein the main conveyor and the auxiliary conveyor can be built as modules to permit inclusion of any selected number of auxiliary conveyors as well as the elimination of unwanted auxiliary conveyors should they no longer be needed at some future time, a novel conveyor system having traffic control gates that can be positioned directly alongside the main conveyor and the auxiliary conveyor, a novel conveyor system having traffic control gates wherein two puck rotating mechanisms can be incorporated in a single gate operating from a single motor, a novel conveyor system having utility service connected to column supports for the conveyor for convenient access to such utility service and convenient installation of such utility service, and a novel conveyor system that provides common transport of sample tubes to different clinical apparatus and provides for the bypassing of such clinical apparatus if tests are not required at a particular clinical test apparatus.

In view of the above, it will be seen that the several objects of the invention are achieved and other advantageous results obtained.

As various changes can be made in the above constructions without departing from the scope of the invention, it is intended that all matter contained in the above description or shown in the accompanying drawings shall be interpreted as illustrative and not in a limiting sense.

What is claimed is:

1. A conveyor system for clinical test apparatus comprising,
    a) a main transport conveyor defining a closed circuit path of travel in a generally horizontal plane, the closed circuit path of travel permitting objects on the conveyor to repeat the path of travel when the conveyor is moving in one direction, the closed circuit path of travel including a straight line path and a curved path,
    b) an auxiliary conveyor defining a straight line path of travel in a generally horizontal plane, the straight line path of travel permitting objects on the conveyor to move from one point to another without retracing any point of travel when the conveyor is moving in said one direction, said auxiliary conveyor having an upstream end and a downstream end relative to said one direction of movement,
    c) said auxiliary conveyor being positioned alongside the straight line path of travel of said first transport conveyor to run in the same direction as said first conveyor,
    d) segregation means between the straight line path of said main transport conveyor and said auxiliary conveyor for normally preventing objects from said transport conveyor from moving onto said auxiliary conveyor and vice versa,
    e) said segregation means including first and second openings spaced a predetermined linear distance from each other along said straight line path,
    f) a divert gate device provided at one of said openings proximate an upstream end of said auxiliary conveyor, said divert gate device having diversion means for diverting movement of objects on said main transport conveyor through said one of said openings in said segregation means to said auxiliary conveyor,
    g) an interface gate provided downstream of said one opening and upstream of said other opening in said segregation means, and
    h) said other opening providing a flow path that leads directly from said auxiliary conveyor to said main transport conveyor, wherein said divert gate has a first protractible and retractable hold back means having a protracted position for holding back the movement of objects on said main transport conveyor as said objects approach said divert gate, said first hold back means being operable independently of said diversion means, and wherein said divert gate includes a second protractible and retractible hold back means having a protracted position for holding back the movement of objects on said main transport conveyor, said first and second hold back means being spaced a predetermined amount from each other to constitute a singulator means for singulating an object.

2. The conveyor system as claimed in claim 1 including automatic label reading means co-operable with said divert gate and said singulator means for reading a label on an object that is singulated at said divert gate by said first and second hold back means.

* * * * *